(12) United States Patent
Matsumoto et al.

(10) Patent No.: US 10,337,009 B2
(45) Date of Patent: Jul. 2, 2019

(54) SINGLE-STRANDED NUCLEIC ACID MOLECULE FOR INHIBITING TGF-β1 EXPRESSION

(71) Applicant: BONAC CORPORATION, Kurume-shi, Fukuoka (JP)

(72) Inventors: Takahiro Matsumoto, Kurume (JP); Hidekazu Toyofuku, Kurume (JP)

(73) Assignee: BONAC CORPORATION, Kurume (JP)

(*) Notice: Subject to any disclaimer, the term of this patent is extended or adjusted under 35 U.S.C. 154(b) by 0 days.

(21) Appl. No.: 15/536,006

(22) PCT Filed: Dec. 15, 2015

(86) PCT No.: PCT/JP2015/085116
§ 371 (c)(1),
(2) Date: Jun. 14, 2017

(87) PCT Pub. No.: WO2016/098782
PCT Pub. Date: Jun. 23, 2016

(65) Prior Publication Data
US 2017/0349902 A1 Dec. 7, 2017

(30) Foreign Application Priority Data

Dec. 15, 2014 (JP) .................. 2014-253148
Dec. 15, 2014 (JP) .................. 2014-253149
Jun. 17, 2015 (JP) .................. 2015-121644
Jun. 17, 2015 (JP) .................. 2015-121647

(51) Int. Cl.
| A61K 48/00 | (2006.01) |
| C12N 15/09 | (2006.01) |
| C12N 15/113 | (2010.01) |
| A61K 31/7105 | (2006.01) |

(52) U.S. Cl.
CPC ...... *C12N 15/1136* (2013.01); *A61K 31/7105* (2013.01); *A61K 48/00* (2013.01); *C12N 15/09* (2013.01); *C12N 15/113* (2013.01); *C12N 2310/14* (2013.01)

(58) Field of Classification Search
CPC ........ C12N 2310/321; C12N 2310/322; C12N 2310/3521; C12N 2310/3533; C12N 2310/113; C12N 2310/3515; A61K 38/00; C12Q 1/6886
USPC ....... 435/6.1, 91.1, 91.31, 325, 455; 514/44; 536/23.1, 24.5
See application file for complete search history.

(56) References Cited

U.S. PATENT DOCUMENTS

2005/0119202 A1 6/2005 Kreutzer et al.
2012/0010271 A1 1/2012 Ohgi et al.
2012/0035246 A1 2/2012 Ohgi et al.
2013/0011922 A1* 1/2013 Quay .................. C12N 15/111
                                                                435/366
2013/0217754 A1 8/2013 Gabazza et al.
2017/0067056 A1* 3/2017 Khvorova ............ C12N 15/113

FOREIGN PATENT DOCUMENTS

| EP | 2431466 A1 | 3/2012 | |
| JP | 2007-119396 A | 5/2007 | |
| JP | 2009-516517 A | 4/2009 | |
| JP | WO2012017919 A1 * | 10/2013 | ........... C12N 15/113 |
| WO | WO 2003/035083 A1 | 5/2003 | |
| WO | WO 2007/056826 A1 | 5/2007 | |
| WO | WO 2007/109097 A2 | 9/2007 | |
| WO | WO 2008/109548 A2 | 9/2008 | |
| WO | WO 2011/119887 A1 | 9/2011 | |
| WO | WO 2012/005368 A1 | 1/2012 | |
| WO | WO 2012/017919 A1 | 2/2012 | |
| WO | WO 2012/050181 A1 | 4/2012 | |
| WO | WO 2015/093495 A1 | 6/2015 | |

OTHER PUBLICATIONS

Hamasaki et al (PLoS One, vol. 7, Issue 8, e42655, pp. 1-10.*
Geneseq Database, Geneseq Database Entry for WO 2008/109548, "Human TGFB1 mRNA target sequence for mdRNA SEQ ID: 1354," Accession No. ATM76848 (Nov. 13, 2008).
D'Alessandro-Gabazza et al., "Development and Preclinical Efficacy of Novel Transforming Growth Factor-β1 Short Interfering RNAs for Pulmonary Fibrosis," *Am. J. Respir. Cell. Mol. Biol.*, 46(3): 397-406 (2012).
Hamasaki et al., "Efficacy of a Novel Class of RNA Interference Therapeutic Agents," *PLoS One*, 7(8): e42655 (2012).
Hwang et al., "TGF-β1 siRNA suppresses the tubulointerstitial fibrosis in the kidney of ureteral obstruction," *Exp. Mol. Pathol.*, 81(1): 48-54 (2006).
Liu et al., "Antagonism of transforming growth factor-β signaling inhibits fibrosis-related genes," *Biotechnol. Lett.*, 27(20): 1609-1615 (2005).

(Continued)

*Primary Examiner* — Jane J Zara
(74) *Attorney, Agent, or Firm* — Leydig, Voit & Mayer, Ltd.

(57) ABSTRACT

The invention provides a single-stranded nucleic acid molecule of (A) or (B) containing a TGF-β1 gene expression inhibitory sequence. The single-stranded nucleic acid molecule (A) consists of region (Xc), linker region (Lx) and region (X) from the 5'-side to the 3'-side, wherein linker region (Lx) has a non-nucleotide structure containing at least one of a pyrrolidine skeleton and a piperidine skeleton, and at least one of region (X) and region (Xc) contains the expression inhibitory sequence. The single-stranded nucleic acid molecule (B) contains region (Xc), linker region (Lx), region (X), region (Y), linker region (Ly) and region (Yc) from the 5'-side to the 3'-side, wherein region (X) and region (Y) are linked to form inner region (Z), region (Xc) is complementary to region (X), region (Yc) is complementary to region (Y), linker region (Lx) and linker region (Ly) each have a non-nucleotide structure containing at least one of a pyrrolidine skeleton and a piperidine skeleton, and inner region (Z) contains the expression inhibitory sequence.

23 Claims, 6 Drawing Sheets
Specification includes a Sequence Listing.

(56) References Cited

OTHER PUBLICATIONS

Takabatake et al., "Exploring RNA interference as a therapeutic strategy for renal disease," *Gene Ther.*, 12(12): 965-973 (2005).
Wang et al., "Inhibition of Smad3 expression decreases collagen synthesis in keloid disease fibroblasts," *J. Plast. Reconstr. Aesthet. Surg.*, 60(11): 1193-1199 (2007).
Xu et al., "Effects of RNA interference targeting transforming growth factor-beta 1 on immune hepatic fibrosis induced by Concanavalin A in mice," *Hepatobiliary Pancreat. Dis. Int.*, 8(3): 300-308 (2009).
Japanese Patent Office, International Search Report in International Application No. PCT/JP2015/085116 (dated Mar. 1, 2016).

* cited by examiner (A)

(B)

(A)

(B)

(A)

(B)

(A)

(B)

(C)

(D)

(A)

(B)

(A)

(B)

SINGLE-STRANDED NUCLEIC ACID MOLECULE FOR INHIBITING TGF-β1 EXPRESSION

CROSS-REFERENCE TO RELATED APPLICATIONS

This patent application is the U.S. national phase of International Patent Application No. PCT/JP2015/085116, filed Dec. 15, 2015, which claims the benefit of Japanese Patent Application No. 2014-253148, filed on Dec. 15, 2014, Japanese Patent Application No. 2014-253149, filed on Dec. 15, 2014, Japanese Patent Application No. 2015-121644, filed Jun. 17, 2015, and Japanese Patent Application No. 2015-121647, filed on Jun. 17, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,917 bytes ASCII (Text) file named "729011UpdatedSequenceListing.txt," created Oct. 29, 2018.

TECHNICAL FIELD

The present invention relates to a nucleic acid molecule that inhibits expression of TGF-β1 gene, a composition containing same and use thereof.

BACKGROUND ART

Pulmonary fibrosis is a disease in which lung tissues are fibrosed by accumulation of excess collagen and other cell matrices. Among the pulmonary fibrosis, idiopathic pulmonary fibrosis is a chronic intractable disease with a median survival time of 3 years on average, and five-year survival rate of 20 to 40%.

Acute lung injury is one kind of acute respiratory disturbances, and is acute respiratory failure showing pulmonary infiltrative shadow. The pathology of acute lung injury is pulmonary edema due to permeability promotion caused by pulmonary capillary endothelial cell and alveolar wall cell damage. The interstitial pulmonary edema, pulmonary alveolar edema and pulmonary collapse increase dead space ventilation ratio and develop hypoxemia.

As the situation stands, an effective treatment method is not available for pulmonary fibrosis and acute lung injury, and the development of an effective therapeutic drug has been desired. It has been reported that the onset of pulmonary fibrosis and acute lung injury involves expression of TGF-β1, and therefore, attempts have been made to inhibit gene expression (patent documents 1-5, non-patent documents 1-6).

As a technique for inhibiting gene expression, for example, RNA interference (RNAi) is known. Inhibition of gene expression by RNA interference is generally carried out, for example, by administering a short double-stranded RNA molecule to a cell or the like. The aforementioned double-stranded RNA molecule is generally called siRNA (small interfering RNA). As regards the aforementioned expression of TGF-β1 gene, siRNA has been studied; however, provision of a more effective nucleic acid molecule has been desired.

In recent years, the present inventors have newly found a more effective single-stranded nucleic acid molecule replacing siRNA (patent documents 6, 7, non-patent document 7).

DOCUMENT LIST

Patent Documents patent document 1: WO 2007/109097
patent document 2: WO 2003/035083
patent document 3: JP-A-2007-119396
patent document 4: National Publication of International Patent Application No. 2009-516517
patent document 5: WO 2012/050181
patent document 6: WO 2012/005368
patent document 7: WO 2012/017919

Non-Patent Document non-patent document 1: Wang et al., J Plast Reconstr Aesthet Surg, 1193-1199, 60, 2007
non-patent document 2: Hwang et al., Exp Mol pathol, 48-54, 81, 2006
non-patent document 3: Takabatake et al., Gene Ther, 965-973, 12, 2005
non-patent document 4: Xu et al., Hepatobiliary Pancreat Dis Int, 300-308, 2009
non-patent document 5: Liu et al., Biothechnol Lett, 1609-1615, 27, 2005
non-patent document 6: Gabazza et al., Am J Respir Cell Mol Biol. 397-406, 46, 2012
non-patent document 7: Hamasaki et al., PLoS ONE, 7(8), e42655, doi:10.1371, 2012

SUMMARY OF THE INVENTION

Problems to be Solved by the Invention

Thus, the present invention aims to provide, based on the structure of the aforementioned nucleic acid molecule found in the earlier invention, a nucleic acid molecule effective for the treatment of diseases involving expression of TGF-β1 such as pulmonary fibrosis, acute lung injury and the like, and a medicament using same.

Means of Solving the Problems

To achieve the aforementioned object, the nucleic acid molecule of the present invention for inhibiting the expression of TGF-β1 gene is characterized in that it contains any of the following nucleotide sequences as a TGF-β1 gene expression inhibitory sequence:

(SEQ ID NO: 1)
5'-AUUUCGUUGUGGGUUUCCACC-3'

(SEQ ID NO: 2)
5'-UGUUAUCCCUGCUGUCACAGG-3'

The composition of the present invention is a composition for inhibiting the expression of TGF-β1 gene, and characteristically contains the above-mentioned nucleic acid molecule of the present invention.

The composition of the present invention is a pharmaceutical composition which characteristically contains the above-mentioned nucleic acid molecule of the present invention.

The expression inhibiting method of the present invention is a method for inhibiting the expression of TGF-β1 gene, which characteristically uses the above-mentioned nucleic acid molecule of the present invention.

The method for treating pulmonary fibrosis of the present invention characteristically includes a step of administering the above-mentioned nucleic acid molecule of the present invention to a patient.

The method for treating acute lung injury of the present invention characteristically includes a step of administering the above-mentioned nucleic acid molecule of the present invention to a patient.

EFFECT OF THE INVENTION

According to the nucleic acid molecule of the present invention, the expression of TGF-β1 gene can be inhibited. Therefore, the present invention is effective for the treatment of diseases caused by the expression of TGF-β1 gene, for example, pulmonary fibrosis, acute lung injury and the like.

DESCRIPTION OF EMBODIMENTS

Figure 1:
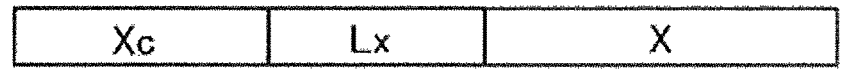
FIG. 1 shows schematic views illustrating an example of the nucleic acid molecule of the present invention.
Figure 1:
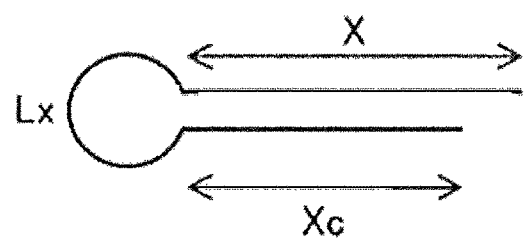

Unless otherwise specified, the terms used in the present specification mean what is generally meant by them in the art.

1. Nucleic Acid Molecule for Inhibiting Expression of TGF-β1 Gene

The nucleic acid molecule of the present invention is, as mentioned above, for inhibiting the expression of TGF-β1 gene, and characteristically contains the following nucleotide sequence as a TGF-β1 gene expression inhibitory sequence:

```
                                            (SEQ ID NO: 1)
        5'-AUUUCGUUGUGGGUUUCCACC-3'

(SEQ ID NO: 2)
        5'-UGUUAUCCCUGCUGUCACAGG-3'
```

The aforementioned expression inhibitory sequence is, for example, a sequence composed of the aforementioned nucleotide sequence, or a sequence containing the aforementioned nucleotide sequence.

The length of the aforementioned expression inhibitory sequence is not particularly limited and is, for example, 18 to 32 base length, preferably 19 to 30 base length, more preferably 19, 20, 21 base length. In the present invention, for example, the numerical value range of the base number discloses all positive integers belonging to the range. For example, an indication of "1 to 4 bases" means disclosure of any of "1, 2, 3, 4 bases" (hereinafter the same).

The single-stranded nucleic acid molecule of the present invention preferably contains, for example, a complementary sequence annealable with the aforementioned expression inhibitory sequence. The aforementioned complementary sequence is, for example, in the same strand as the aforementioned expression inhibitory sequence and forms a single-stranded nucleic acid molecule constituted of one single strand.

The aforementioned complementary sequence only needs to be annealable with, for example, the aforementioned expression inhibitory sequence. The aforementioned complementary sequence may be, for example, a sequence showing 100% complementarity with the aforementioned expression inhibitory sequence, or a sequence showing complementarity of less than 100% within an annealable range. The aforementioned complementarity is not particularly limited and, for example, 90%-100%, 93%-100%, 95%-100%, 98%-100%, 99%-100% or the like.

Examples of the aforementioned complementary sequence include those containing, for example, the following nucleotide sequences.

```
                                            (SEQ ID NO: 3)
        5'-UGGAAACCCACAACGAAAUCU-3'

(SEQ ID NO: 4)
        5'-UGUGACAGCAGGGAUAACACA-3'
```

The aforementioned nucleotide sequence of SEQ ID NO: 3 or 4 is hereinafter referred to as an s nucleotide sequence.

The aforementioned complementary sequence may be, for example, a sequence composed of the aforementioned s nucleotide sequence, or a sequence containing the aforementioned s nucleotide sequence.

The length of the aforementioned complementary sequence is not particularly limited and is, for example, 18-32 base length, preferably 19-30 base length, more preferably 19, 20, 21 base length.

The aforementioned expression inhibitory sequence and the aforementioned complementary sequence may each be, for example, an RNA molecule consisting of ribonucleotide residues alone, or an RNA molecule containing a deoxyribonucleotide residue besides the ribonucleotide residues.

Single-Stranded Nucleic Acid Molecule

As the aforementioned nucleic acid molecule, for example, a form wherein the aforementioned expression inhibitory sequence and the aforementioned complementary sequence are directly or indirectly linked can be mentioned. As the aforementioned direct linkage, for example, a linkage by a phosphodiester bond can be mentioned. As the aforementioned indirect linkage, for example, a linkage via a linker region can be mentioned. The order of linkage of the aforementioned expression inhibitory sequence and the aforementioned complementary sequence is not particularly limited and, for example, the 3'-terminus of the aforementioned expression inhibitory sequence and the 5'-terminus of the aforementioned complementary sequence may be linked, or the 5'-terminus of the aforementioned expression inhibitory sequence and the 3'-terminus of the aforementioned complementary sequence may be linked, with preference given to the former. The aforementioned linker region may be constituted of, for example, nucleotide residues, may be constituted of non-nucleotide residues, or may be constituted of the aforementioned nucleotide residues and non-nucleotide residues. As the aforementioned nucleotide residue, for example, ribonucleotide residue and deoxyribonucleotide residue can be mentioned.

While specific examples of the aforementioned single-stranded nucleic acid molecule are shown below, the present invention is not limited thereto.

As a first form of the aforementioned single-stranded nucleic acid molecule, a molecule wherein a 5'-side region and a 3'-side region are mutually annealed to form a double-stranded structure (stem structure) can be mentioned. This can also be said a form of shRNA (small hairpin RNA or short hairpin RNA). shRNA has a hairpin structure and generally has one stem region and one loop region.

The nucleic acid molecule in this form has a structure containing, for example, region (X), linker region (Lx) and region (Xc), wherein the aforementioned linker region (Lx) is linked between the aforementioned region (X) and the aforementioned region (Xc). A structure wherein the aforementioned region (Xc) is complementary to the aforementioned region (X) is preferable, and specifically, it is preferable that one of the aforementioned region (X) and the aforementioned region (Xc) contains the aforementioned expression inhibitory sequence, and the other contains the aforementioned complementary sequence. Since the aforementioned region (X) and the aforementioned region (Xc) each have any of the aforementioned expression inhibitory sequence and the aforementioned complementary sequence, for example, they can form a stem structure by intramolecular annealing, and the aforementioned linker region (Lx) becomes a loop structure.

The aforementioned nucleic acid molecule may have, for example, the aforementioned region (Xc), the aforementioned linker region (Lx) and the aforementioned region (X) from the 5'-side to the 3'-side in the aforementioned order, or the aforementioned region (Xc), the aforementioned linker region (Lx) and the aforementioned region (X) from the 3'-side to the 5'-side in the aforementioned order. The aforementioned expression inhibitory sequence may be configured in, for example, any of the aforementioned region (X) and the aforementioned region (Xc), and preferably configured on the upstream side of the aforementioned complementary sequence, i.e., 5'-side than the aforementioned complementary sequence.

One embodiment of the nucleic acid molecule in this form is shown in the schematic drawing of FIG. 1. FIG. 1(A) is a schematic drawing of an outline of the order of each region, FIG. 1(B) is a schematic drawing showing that the aforementioned nucleic acid molecule forms a double strand in the aforementioned molecule. As shown in FIG. 1(B), the aforementioned nucleic acid molecule forms a double strand between the aforementioned region (Xc) and the aforementioned region (X), and the aforementioned Lx region has a loop structure according to the length thereof. FIG. 1 shows the order of the aforementioned regions and the positional relationship of each region forming a double strand and, for example, the length of each region, the shape of the aforementioned linker region (Lx) and the like are not limited to these.

In the aforementioned nucleic acid molecule, the base number of the aforementioned region (Xc) and the aforementioned region (X) is not particularly limited. While examples of the length of each region are shown below, the present invention is not limited thereto.

In the aforementioned nucleic acid molecule, the relationship between the base number (X) of the aforementioned region (X) and the base number (Xc) of the aforementioned region (Xc) satisfies, for example, the conditions of the following (3) or (5). In the former case, specifically, it satisfies, for example, the conditions of the following (11).

$$X > Xc \quad (3)$$

$$X - Xc = 1 \text{ to } 10, \text{preferably } 1, 2 \text{ or } 3,$$

more preferably 1 or 2 (11)

$$X = Xc \quad (5)$$

When the aforementioned region (X) or the aforementioned region (Xc) contains the aforementioned expression inhibitory sequence, the aforementioned region may be, for example, a region constituted only of the aforementioned expression inhibitory sequence, or a region containing the aforementioned expression inhibitory sequence. The base number of the aforementioned expression inhibitory sequence is, for example, as described above. The region of the aforementioned expression inhibitory sequence may further have, for example, an additional sequence at the 5'-side and/or the 3'-side of the aforementioned expression inhibitory sequence. The base number of the aforementioned additional sequence is, for example, 1-31, preferably 1-21, more preferably 1-11.

The base number of the aforementioned region (Xc) is not particularly limited. When the aforementioned region (X) contains the aforementioned expression inhibitory sequence, the lower limit of Xc is, for example, 19. The upper limit thereof is, for example, 50, preferably 30, more preferably 25. Specific examples of the base number of the aforementioned region (Xc) is, for example, 19-50, preferably 19-30, more preferably 19-25.

The base number of the aforementioned region (X) is not particularly limited. The lower limit thereof is, for example, 19, preferably 20, more preferably 21. The upper limit thereof is, for example, 50, more preferably 40, further preferably 30.

The aforementioned linker region (Lx) is preferably a structure free of self-annealing in the region of itself.

When the aforementioned region (Lx) contains a nucleotide residue as mentioned above, the length thereof is not particularly limited. The aforementioned linker region (Lx) preferably has a length, for example, permitting the aforementioned region (X) and the aforementioned region (Xc) to form a double strand. The lower limit of the base number of the aforementioned linker region (Lx) is, for example, 1, preferably 2, more preferably 3, and the upper limit thereof is, for example, 100, preferably 80, more preferably 50.

The full length of the aforementioned nucleic acid molecule is not particularly limited. In the aforementioned nucleic acid molecule, the lower limit of the total of the aforementioned base number (base number of full length) is, for example, 38, preferably 42, more preferably 50, further preferably 51, particularly preferably 52, and the upper limit thereof is, for example, 300, preferably 200, more preferably 150, further preferably 100, particularly preferably 80. In the aforementioned nucleic acid molecule, the lower limit of the total of the base number excluding the aforementioned linker region (Lx) is, for example, 38, preferably 42, more preferably 50, further preferably 51, particularly preferably 52, and the upper limit is, for example, 300, preferably 200, more preferably 150, further preferably 100, particularly preferably 80.

As a second form of the aforementioned single-stranded nucleic acid molecule is a molecule in which the 5'-side region and the 3'-side region are separately annealed in the molecule to form two double-stranded structures (stem structures) can be mentioned.

A nucleic acid molecule in this form is preferably a structure containing, for example, 5'-side region (Xc), inner region (Z) and 3'-side region (Yc) from the 5'-side to the 3'-side in the aforementioned order, wherein the aforementioned inner region (Z) is constituted by the linkage of the inner 5'-side region (X) and the inner 3'-side region (Y), the aforementioned 5'-side region (Xc) is complementary to the aforementioned inner 5'-side region (X), and the aforementioned 3'-side region (Yc) is complementary to the aforementioned inner 3'-side region (Y). At least one of the aforementioned inner region (Z), the aforementioned 5'-side region (Xc) and the aforementioned 3'-side region (Yc) preferably contains the aforementioned expression inhibitory sequence. Specifically, when the aforementioned inner 5'-side region (X) of the aforementioned inner region (Z) has the aforementioned expression inhibitory sequence, the aforementioned 5'-side region (Xc) preferably has the aforementioned complementary sequence, and when the aforementioned inner 3'-side region (Y) of the aforementioned inner region (Z) has the aforementioned expression inhibitory sequence, the aforementioned 3'-side region (Yc) preferably has the aforementioned complementary sequence. When the aforementioned 5'-side region (Xc) has the aforementioned expression inhibitory sequence, the aforementioned inner 5'-side region (X) of the aforementioned inner region (Z) preferably has the aforementioned complementary sequence, and when the aforementioned 3'-side region (Yc) has the aforementioned expression inhibitory sequence, the aforementioned inner 3'-side region (Y) of the aforementioned inner region (Z) preferably has the aforementioned complementary sequence.

In the aforementioned nucleic acid molecule, the aforementioned 5'-side region (Xc) is complementary to the aforementioned inner 5'-side region (X), and the aforementioned 3'-side region (Yc) is complementary to the aforementioned inner 3'-side region (Y). Therefore, a double strand can be formed at the 5'-side when the aforementioned region (Xc) folds back toward the aforementioned region (X), and the aforementioned region (Xc) and the aforementioned region (X) are self-annealed, and also, a double strand can be formed at the 3'-side when the aforementioned region (Yc) folds back toward the aforementioned region (Y), and the aforementioned region (Yc) and the aforementioned region (Y) are self-annealed.

In the aforementioned inner region (Z), the aforementioned inner 5'-region (X) and the aforementioned inner 3'-region (Y) are linked, as mentioned above. The aforementioned region (X) and the aforementioned region (Y) are, for example, directly linked, and does not have an intervening sequence therebetween. The aforementioned inner region (Z) is expressed by "constituted by the linkage of the aforementioned inner 5'-side region (X) and the aforementioned inner 3'-side region (Y)" to show the sequence relationship between the aforementioned 5'-side region (Xc) and the aforementioned 3'-side region (Yc). It does not limit that, in the aforementioned inner region (Z), the aforementioned 5'-side region (Xc) and the aforementioned 3'-side region (Yc) are, for example, separate and independent regions in the use of the aforementioned nucleic acid molecule. That is, for example, when the aforementioned inner region (Z) has the aforementioned expression inhibitory sequence, the aforementioned expression inhibitory sequence may be configured over the aforementioned region (X) and the aforementioned region (Y) in the aforementioned inner region (Z).

In the aforementioned nucleic acid molecule, the aforementioned 5'-side region (Xc) and the aforementioned inner 5'-side region (X) may be, for example, directly or indirectly linked. In the former case, as the direct linkage, for example, linkage by a phosphodiester bond can be mentioned. In the latter case, for example, a form wherein linker region (Lx) is present between the aforementioned region (Xc) and the aforementioned region (X), and the aforementioned region (Xc) and the aforementioned region (X) are linked via the aforementioned linker region (Lx) can be mentioned.

In the aforementioned nucleic acid molecule, the aforementioned 3'-side region (Yc) and the aforementioned inner 3'-side region (Y) may be, for example, directly or indirectly linked. In the former case, as the direct linkage, for example, linkage by a phosphodiester bond can be mentioned. In the latter case, for example, a form wherein linker region (Ly) is present between the aforementioned region (Yc) and the aforementioned region (Y), and the aforementioned region (Yc) and the aforementioned region (Y) are linked via the aforementioned linker region (Ly) can be mentioned.

The aforementioned nucleic acid molecule may have, for example, both or either one of the aforementioned linker region (Lx) and the aforementioned linker region (Ly). In the latter case, for example, a form wherein the aforementioned linker region (Lx) is present between the aforementioned 5'-side region (Xc) and the aforementioned inner 5'-side region (X), and the aforementioned linker region (Ly) is absent between the aforementioned 3'-side region (Yc) and the aforementioned inner 3'-side region (Y), namely, the aforementioned region (Yc) and the aforementioned region (Y) are directly linked, can be mentioned. In the latter case, for example, a form wherein the aforementioned linker region (Ly) is present between the aforementioned 3'-side region (Yc) and the aforementioned inner 3'-side region (Y), and the aforementioned linker region (Lx) is absent between the aforementioned 5'-side region (Xc) and the aforementioned inner 5'-side region (X), namely, the aforementioned region (Xc) and the aforementioned region (X) are directly linked, can be mentioned.

The aforementioned linker region (Lx) and the aforementioned linker region (Ly) are each preferably a structure free of self-annealing in the region of themselves.

Figure 2:
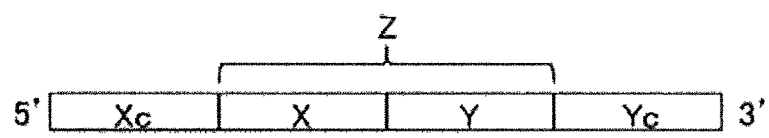
FIG. 2 shows schematic views illustrating another example of the nucleic acid molecule of the present invention.
Figure 2:
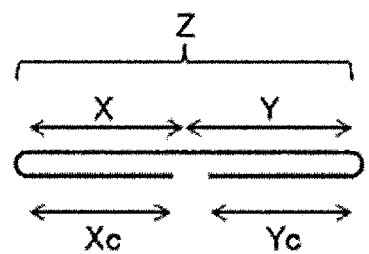

As regards a nucleic acid molecule in this form, one embodiment free of the aforementioned linker region is shown in the schematic drawing of FIG. 2. FIG. 2(A) is a schematic drawing of an outline of the order of each region from the 5'-side to the 3'-side with regard to the aforementioned nucleic acid molecule, FIG. 2(B) is a schematic drawing showing that the aforementioned nucleic acid molecule forms double strands in the aforementioned molecule. As shown in FIG. 2(B), in the aforementioned nucleic acid molecule, the aforementioned 5'-side region (Xc) folds back, and a double strand is formed between the aforementioned 5'-side region (Xc) and the aforementioned inner 5'-side region (X) and the aforementioned 3'-side region (Yc) folds back, and a double strand is formed between the aforementioned 3'-side region (Yc) and the aforementioned inner 3'-side region (Y). FIG. 2 shows the order of each region and the positional relationship of each region forming a double strand and, for example, the length of each region and the like are not limited to these.

Figure 3:
FIG. 3 shows schematic views illustrating another example of the nucleic acid molecule of the present invention.
Figure 3:
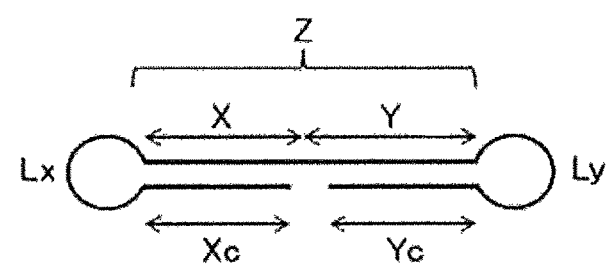

As regards the aforementioned nucleic acid molecule in this form, one embodiment having the aforementioned linker region is shown in the schematic drawing of FIG. 3.

FIG. 3(A) is a schematic drawing of, as one embodiment, an outline of the order of each region from the 5'-side to the 3'-side with regard to the aforementioned nucleic acid molecule, FIG. 3(B) is a schematic drawing showing that the aforementioned nucleic acid molecule forms double strands in the aforementioned molecule. As shown in FIG. 3(B), in the aforementioned nucleic acid molecule, a double strand is formed between the aforementioned 5'-side region (Xc) and the aforementioned inner 5'-side region (X), and between the aforementioned inner 3'-side region (Y) and the aforementioned 3'-side region (Yc), and the aforementioned Lx region and the aforementioned Ly region have loop structures. FIG. 3 shows the order of each region and the positional relationship of each region forming a double strand and, for example, the length of each region and the like are not limited to these.

In the aforementioned nucleic acid molecule, the base numbers of the aforementioned 5'-side region (Xc), the aforementioned inner 5'-side region (X), the aforementioned inner 3'-side region (Y) and the aforementioned 3'-side region (Yc) are not particularly limited and, for example, as described below.

The aforementioned 5'-side region (Xc) may be, as mentioned above, complementary to, for example, the whole region of the aforementioned inner 5'-side region (X). In this case, the aforementioned region (Xc) has, for example, the same base length as that of the aforementioned region (X), and is preferably composed of a base sequence complementary to the whole region of from the 5'-terminus to the 3'-terminus of the aforementioned region (X). The aforementioned region (Xc) more preferably has the same base length as that of the aforementioned region (X), and all bases of the aforementioned region (Xc) are complementary to all bases of the aforementioned region (X), namely, for example, preferably completely complementary thereto. This is not limitative and, for example, 1 to several (2, 3, 4 or 5) bases may be noncomplementary, as mentioned above.

The aforementioned 5'-side region (Xc) may be, as mentioned above, complementary to, for example, a partial region of the aforementioned inner 5'-side region (X). In this case, the aforementioned region (Xc) has, for example, the same base length as a partial region of the aforementioned region (X), that is, preferably composed of a base sequence having a base length shorter than that of the aforementioned region (X) by not less than one base. The aforementioned region (Xc) more preferably has the same base length as that of the aforementioned partial region of the aforementioned region (X), and all bases of the aforementioned region (Xc) are complementary to all bases of the aforementioned partial region of the aforementioned region (X), namely, for example, preferably completely complementary thereto. The aforementioned partial region of the aforementioned region (X) is, for example, preferably a region (segment) composed of a base sequence continuous from the base (first base) of the 5'-terminus in the aforementioned region (X).

The aforementioned 3'-side region (Yc) may be, as mentioned above, complementary to, for example, the whole region of the aforementioned inner 3'-side region (Y). In this case, the aforementioned region (Yc) has, for example, the same base length as that of the aforementioned region (Y), and is preferably composed of a base sequence complementary to the whole region of from the 5'-terminus to the 3'-terminus of the aforementioned region (Y). The aforementioned region (Yc) more preferably has the same base length as that of the aforementioned region (Y), and all bases of the aforementioned region (Yc) are complementary to all bases of the aforementioned region (Y), namely, for example, preferably completely complementary thereto. This is not limitative and, for example, 1 to several (2, 3, 4 or 5) bases may be noncomplementary, as mentioned above.

The aforementioned 3'-side region (Yc) may be, as mentioned above, complementary to, for example, a partial region of the aforementioned inner 3'-side region (Y). In this case, the aforementioned region (Yc) has, for example, the same base length as a partial region of the aforementioned region (Y), that is, preferably composed of a base sequence having a base length shorter than that of the aforementioned region (Y) by not less than one base. The aforementioned region (Yc) more preferably has the same base length as that of the aforementioned partial region of the aforementioned region (Y), and all bases of the aforementioned region (Yc) are complementary to all bases of the aforementioned partial region of the aforementioned region (Y), namely, for example, preferably completely complementary thereto. The aforementioned partial region of the aforementioned region (Y) is, for example, preferably a region (segment) composed of a base sequence continuous from the base (first base) of the 3'-terminus in the aforementioned region (Y).

In the aforementioned nucleic acid molecule, the relationship between the base number (Z) of the aforementioned inner region (Z), and the base number (X) of the aforementioned inner 5'-side region (X) and the base number (Y) of the aforementioned inner 3'-side region (Y), and the relationship between the base number (Z) of the aforementioned inner region (Z), and the base number (Xc) of the aforementioned inner 5'-side region (Xc) and the base number (Yc) of the aforementioned inner 3'-side region (Yc) satisfy, for example, the conditions of the following formulas (1) and (2):

$$Z = X + Y \qquad (1)$$

$$Z \geq Xc + Yc \qquad (2)$$

In the nucleic acid molecule of the present invention, the relationship in the length between the base number (X) of the aforementioned inner 5'-side region (X) and the base number (Y) of the aforementioned inner 3'-side region (Y) is not particularly limited and, for example, may satisfy the conditions of any of the following formulas:

$$X = Y \qquad (19)$$

$$X < Y \qquad (20)$$

$$X > Y \qquad (21)$$

In the aforementioned nucleic acid molecule, the relationship among the base number (X) of the aforementioned inner 5'-side region (X), the base number (Xc) of the aforementioned 5'-side region (Xc), the base number (Y) of the aforementioned inner 3'-side region (Y) and the base number (Yc) of the aforementioned 3'-side region (Yc) satisfies, for example, the conditions of any of the following (a) to (d):

(a) satisfies the conditions of the following formulas (3) and (4):

$$X > Xc \qquad (3)$$

$$Y = Yc \qquad (4)$$

(b) satisfies the conditions of the following formulas (5) and (6):

$$X = Xc \qquad (5)$$

$$Y > Yc \qquad (6)$$

(c) satisfies the conditions of the following formulas (7) and (8):

$$X > Xc \quad (7)$$

$$Y > Yc \quad (8)$$

(d) satisfies the conditions of the following formulas (9) and (10):

$$X = Xc \quad (9)$$

$$Y = Yc \quad (10)$$

In the aforementioned (a) to (d), a difference between the base number (X) of the aforementioned inner 5'-side region (X) and the base number (Xc) of the aforementioned 5'-side region (Xc), and a difference between the base number (Y) of the aforementioned inner 3'-side region (Y) and the base number (Yc) of the aforementioned 3'-side region (Yc) preferably satisfy, for example, the following conditions.

(a) satisfies the conditions of the following formulas (11) and (12):

$$X - Xc = 1 \text{ to } 10, \text{preferably } 1,2,3 \text{ or } 4,$$

$$\text{more preferably } 1,2 \text{ or } 3 \quad (11)$$

$$Y - Yc = 0 \quad (12)$$

(b) satisfies the conditions of the following formulas (13) and (14):

$$X - Xc = 0 \quad (13)$$

$$Y - Yc = 1 \text{ to } 10, \text{preferably } 1,2,3 \text{ or } 4,$$

$$\text{more preferably } 1,2 \text{ or } 3 \quad (14)$$

(c) satisfies the conditions of the following formulas (15) and (16):

$$X - Xc = 1 \text{ to } 10, \text{preferably}, 1,2 \text{ or } 3,$$

$$\text{more preferably } 1 \text{ or } 2 \quad (15)$$

$$Y - Yc = 1 \text{ to } 10, \text{preferably}, 1,2 \text{ or } 3,$$

$$\text{more preferably } 1 \text{ or } 2 \quad (16)$$

(d) satisfies the conditions of the following formulas (17) and (18):

$$X - Xc = 0 \quad (17)$$

$$Y - Yc = 0 \quad (18)$$

Figure 4:
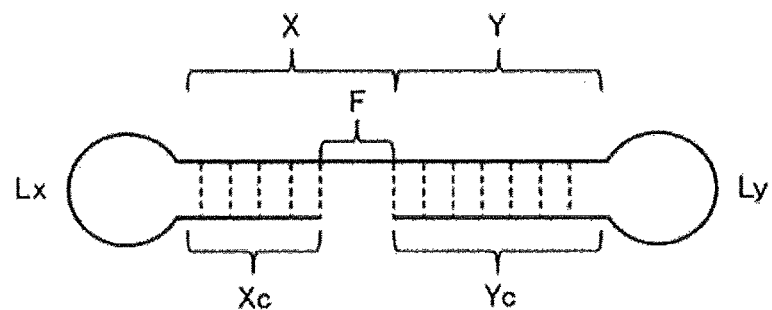
FIG. 4 shows schematic views illustrating another example of the nucleic acid molecule of the present invention.
Figure 4:
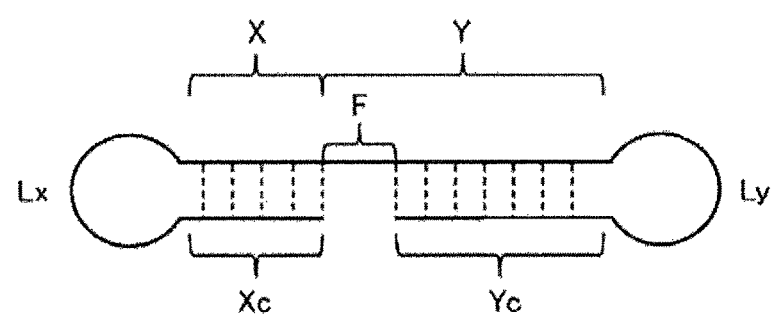
Figure 4:
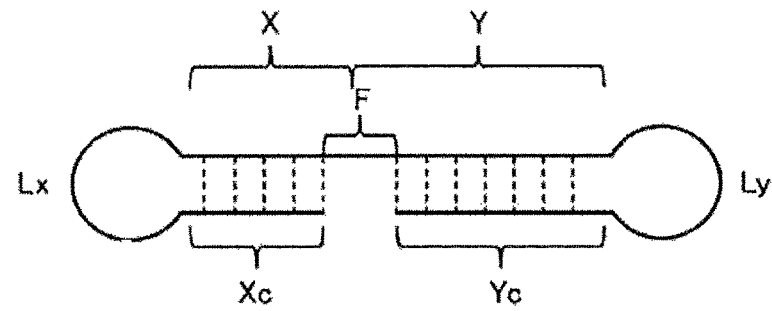
Figure 4:
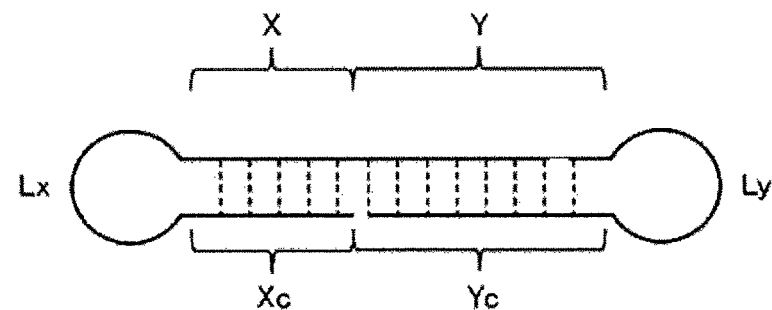

In the nucleic acid molecules of the aforementioned (a) to (d), one embodiment of each structure is shown in the schematic drawing of FIG. 4. FIG. 4 shows a nucleic acid molecule containing the aforementioned linker region (Lx) and the aforementioned linker region (Ly), wherein (A) is the nucleic acid molecule of the aforementioned (a), (B) is the nucleic acid molecule of the aforementioned (b), (C) is the nucleic acid molecule of the aforementioned (c), and (D) is the nucleic acid molecule of the aforementioned (d). In FIG. 4, the dotted lines show double strands formed by self-annealing. In the nucleic acid molecules of FIG. 4, the base number (X) of the aforementioned inner 5'-side region (X) and the base number (Y) of the aforementioned inner 3'-side region (Y) are shown by "X<Y" of the aforementioned formula (20). However, it is not limited thereto, and may be "X=Y" of the aforementioned formula (19) or "X>Y" of the aforementioned formula (21), as mentioned above. FIG. 4 is a schematic drawing showing the relationship between the aforementioned inner 5'-side region (X) and the aforementioned 5'-side region (Xc), and the relationship between the aforementioned inner 3'-side region (Y) and the aforementioned 3'-side region (Yc) and, for example, the length, shape and the like of each region are not limited to these, and the presence or absence of the linker region (Lx) and linker region (Ly) is not limited thereto.

The nucleic acid molecules of the aforementioned (a) to (c) have a structure wherein, for example, the aforementioned 5'-side region (Xc) and the aforementioned inner 5'-side region (X), and the aforementioned 3'-side region (Yc) and the aforementioned inner 3'-side region (Y) each form a double strand, due to which a base cannot align with the aforementioned 5'-side region (Xc) or the aforementioned 3'-side region (Yc) in the aforementioned inner region (Z). It can also be said a structure having a base that does not form a double strand. In the aforementioned inner region (Z), the aforementioned base incapable of alignment (also a base that does not form a double strand) is hereinafter to be referred to as a "unpaired base". In FIG. 4, the region of the aforementioned unpaired base is indicated with "F". The base number of the aforementioned region (F) is not particularly limited. The base number (F) of the aforementioned region (F) is, for example, the base number of "X−Xc" for the nucleic acid molecule of the aforementioned (a), the base number of "Y−Yc" for the nucleic acid molecule of the aforementioned (b), and the total of the base number of "X−Xc" and the base number of "Y−Yc" for the nucleic acid molecule of the aforementioned (c).

On the other hand, the nucleic acid molecule of the aforementioned (d) has a structure wherein, for example, the whole region of the aforementioned inner region (Z) is aligned with the aforementioned 5'-side region (Xc) and the aforementioned 3'-side region (Yc). It can also be said a structure in which the whole region of the aforementioned inner region (Z) forms a double strand. In the nucleic acid molecule of the aforementioned (d), the 5'-terminus of the aforementioned 5'-side region (Xc) and the 3'-terminus of the aforementioned 3'-side region (Yc) are not linked.

While the examples of the length of each region in the aforementioned nucleic acid molecule are shown below, the present invention is not limited thereto.

The total base number of the aforementioned unpaired base (F) in the aforementioned 5'-side region (Xc), the aforementioned 3'-side region (Yc), and the aforementioned inner region (Z) is the base number of the aforementioned inner region (Z). Therefore, the length of the aforementioned 5'-side region (Xc) and the aforementioned 3'-side region (Yc) can be appropriately determined according to, for example, the length of the aforementioned inner region (Z), the number (F) of the aforementioned unpaired base and the position thereof.

The base number of the aforementioned inner region (Z) is, for example, not less than 19. The lower limit of the aforementioned base number is, for example, 19, preferably 20, more preferably 21. The upper limit of the aforementioned base number is, for example, 50, preferably 40, more preferably 30. Specific examples of the base number of the aforementioned inner region (Z) include 19, 20, 21, 22, 23, 24, 25, 26, 27, 28, 29 and 30.

When the aforementioned inner region (Z) contains the aforementioned expression inhibitory sequence, the aforementioned inner region (Z) may be, for example, a region constituted only of the aforementioned expression inhibitory sequence, or a region containing the aforementioned expression inhibitory sequence. The base number of the aforementioned expression inhibitory sequence is, for example, as described above. When the aforementioned inner region (Z)

contains the aforementioned expression inhibitory sequence, an additional sequence may be further added at the 5'-side and/or the 3'-side of the aforementioned expression inhibitory sequence. The base number of the aforementioned additional sequence is, for example, 1-31, preferably 1-21, more preferably 1-11, further preferably 1-7.

The base number of the aforementioned 5'-side region (Xc) is, for example, 1-29, preferably 1-11, more preferably 1-7, further preferably 1-4, particularly preferably 1, 2, 3. When the aforementioned inner region (Z) or the aforementioned 3'-side region (Yc) contains the aforementioned expression inhibitory sequence, for example, these base numbers are preferable. As a specific example, when the base number of the aforementioned inner region (Z) is 19-30 (e.g., 19), the base number of the aforementioned 5'-side region (Xc) is, for example, 1-11, preferably 1-7, more preferably 1-4, further preferably 1, 2, 3.

When the aforementioned 5'-side region (Xc) contains the aforementioned expression inhibitory sequence, the aforementioned 5'-side region (Xc) may be, for example, a region constituted only of the aforementioned expression inhibitory sequence, or a region containing the aforementioned expression inhibitory sequence. The length of the aforementioned expression inhibitory sequence is, for example, as described above. When the aforementioned 5'-side region (Xc) contains the aforementioned expression inhibitory sequence, an additional sequence may be further added at the 5'-side and/or the 3'-side of the aforementioned expression inhibitory sequence. The base number of the aforementioned additional sequence is, for example, 1-11, preferably 1-7.

The base number of the aforementioned 3'-side region (Yc) is, for example, 1-29, preferably 1-11, more preferably 1-7, further preferably 1-4, particularly preferably 1, 2, 3. When the aforementioned inner region (Z) or the aforementioned 5'-side region (Xc) contains the aforementioned expression inhibitory sequence, for example, these base numbers are preferable. As a specific example, when the base number of the aforementioned inner region (Z) is 19-30 (e.g., 19), the base number of the aforementioned 3'-side region (Yc) is, for example, 1-11, preferably 1-7, more preferably 1-4, further preferably 1, 2, 3.

When the aforementioned 3'-side region (Yc) contains the aforementioned expression inhibitory sequence, the aforementioned 3'-side region (Yc) may be, for example, a region constituted only of the aforementioned expression inhibitory sequence, or a region containing the aforementioned expression inhibitory sequence. The length of the aforementioned expression inhibitory sequence is, for example, as described above. When the aforementioned 3'-side region (Yc) contains the aforementioned expression inhibitory sequence, an additional sequence may be further added at the 5'-side and/or the 3'-side of the aforementioned expression inhibitory sequence. The base number of the aforementioned additional sequence is, for example, 1-11, preferably 1-7.

As mentioned above, the base number of the aforementioned inner region (Z), the aforementioned 5'-side region (Xc) and the aforementioned 3'-side region (Yc) can be expressed by, for example, "Z≥Xc+Yc" of the aforementioned formula (2). A specific example of the base number of "Xc+Yc" is the same as that of the aforementioned inner region (Z), or smaller than that of the aforementioned inner region (Z). In the latter case, "Z−(Xc+Yc)" is, for example, 1-10, preferably 1-4, more preferably 1, 2 or 3. The aforementioned "Z−(Xc+Yc)" corresponds to the base number (F) of the region (F) of the aforementioned unpaired base in the aforementioned inner region (Z).

When the aforementioned linker region (Lx) and the aforementioned linker region (Ly) contain a nucleotide residue as mentioned above, the length thereof is not particularly limited. The aforementioned linker region (Lx) preferably has a length, for example, permitting the aforementioned inner 5'-side region (X) and the aforementioned 5'-side region (Xc) to form a double strand, and the aforementioned linker region (Ly) preferably has a length, for example, permitting the aforementioned inner 3'-side region (Y) and the aforementioned 3'-side region (Yc) to form a double strand. The length of the aforementioned linker region (Lx) and the aforementioned linker region (Ly) may be, for example, the same or different, and the base sequence thereof may also be the same or different. The lower limit of the base number of the aforementioned linker region (Lx) and the aforementioned linker region (Ly) is, for example, 1, preferably 2, more preferably 3, and the upper limit thereof is, for example, 100, preferably 80, more preferably 50. Specific examples of the base number of each of the aforementioned linker regions include, but are not limited to, 1-50, 1-30, 1-20, 1-10, 1-7, 1-4 and the like.

The full length of the aforementioned nucleic acid molecule is not particularly limited. In the aforementioned nucleic acid molecule, the lower limit of the total of the aforementioned base number (base number of full length) is, for example, 38, preferably 42, more preferably 50, further preferably 51, particularly preferably 52, and the upper limit thereof is, for example, 300, preferably 200, more preferably 150, further preferably 100, particularly preferably 80. In the aforementioned nucleic acid molecule, the lower limit of the total of the base number excluding the aforementioned linker region (Lx) and linker region (Ly) is, for example, 38, preferably 42, more preferably 50, further preferably 51, particularly preferably 52, and the upper limit is, for example, 300, preferably 200, more preferably 150, further preferably 100, particularly preferably 80.

In a nucleic acid molecule in this form, for example, the 5'-terminus and the 3'-terminus may or may not be bonded. In the former case, the nucleic acid molecule in this form is a cyclic single-stranded nucleic acid molecule. In the latter case, the nucleic acid molecule in this form preferably has, for example, a non-phosphoric acid group at the 5'-terminus since it can maintain the both termini to be unbound.

As a third form of the aforementioned single-stranded nucleic acid molecule, a molecule in which the aforementioned linker region is a non-nucleotide structure can be mentioned.

As regards this form, the aforementioned explanations apply except for the nucleic acid molecules of the aforementioned first form and the aforementioned second form wherein the aforementioned linker region (Lx) and/or the aforementioned linker region (Ly) have/has a non-nucleotide structure.

The aforementioned non-nucleotide structure is not particularly limited and, for example, polyalkylene glycol, pyrrolidine skeleton, piperidine skeleton and the like can be mentioned. As the aforementioned polyalkylene glycol, for example, polyethylene glycol can be mentioned.

As the aforementioned pyrrolidine skeleton, for example, the skeleton of a pyrrolidine derivative, wherein one or more carbons constituting the 5-membered ring of pyrrolidine are substituted, can be mentioned. When the carbon is substituted, it is preferably, for example, a carbon atom other than C-2 carbon. The aforementioned carbon may be, for example, substituted by nitrogen, oxygen or sulfur. The aforementioned pyrrolidine skeleton may also contain, for example, in the 5-membered ring of pyrrolidine, for example, a carbon-carbon double bond or a carbon-nitrogen double bond. In the aforementioned pyrrolidine skeleton, the carbon and nitrogen constituting the 5-membered ring of pyrrolidine may be bonded to, for example, hydrogen or the below-mentioned substituent. The aforementioned linker region (Lx) can be bonded to the aforementioned region (X) and the aforementioned region (Xc), and aforementioned linker region (Ly) can be bonded to the aforementioned region (Y) and the aforementioned region (Yc), via any group of the aforementioned pyrrolidine skeleton. It is any one carbon atom or nitrogen of the aforementioned 5-membered ring, preferably, the 2-position carbon (C-2) or nitrogen of the aforementioned 5-membered ring. Examples of the aforementioned pyrrolidine skeleton include proline skeleton, prolinol skeleton and the like. The aforementioned proline skeleton and prolinol skeleton and the like are also superior in the safety since they are, for example, substances present in living organisms and reductants thereof.

As the aforementioned piperidine skeleton, for example, the skeleton of a piperidine derivative, wherein one or more carbons constituting the 6-membered ring of piperidine are substituted, can be mentioned. When the carbon is substituted, it is preferably, for example, a carbon atom other than C-2 carbon. The aforementioned carbon may be, for example, substituted by nitrogen, oxygen or sulfur. The aforementioned piperidine skeleton may also contain, for example, in the 6-membered ring of piperidine, for example, a carbon-carbon double bond or a carbon-nitrogen double bond. In the aforementioned piperidine skeleton, the carbon and nitrogen constituting the 6-membered ring of piperidine may be bonded to, for example, a hydrogen group or the below-mentioned substituent. The aforementioned linker region (Lx) can be bonded to the aforementioned region (X) and the aforementioned region (Xc), and aforementioned linker region (Ly) can be bonded to the aforementioned region (Y) and the aforementioned region (Yc), via any group of the aforementioned piperidine skeleton. It is any one carbon atom or nitrogen of the aforementioned 6-membered ring, more preferably, the 2-position carbon (C-2) or nitrogen of the aforementioned 6-membered ring.

Each of the aforementioned linker regions may be composed of, for example, the non-nucleotide residue(s) having the aforementioned non-nucleotide structure only, or may contain the non-nucleotide residue(s) having the aforementioned non-nucleotide structure and the nucleotide residue(s).

The aforementioned linker region is represented, for example, by the following formula (I):

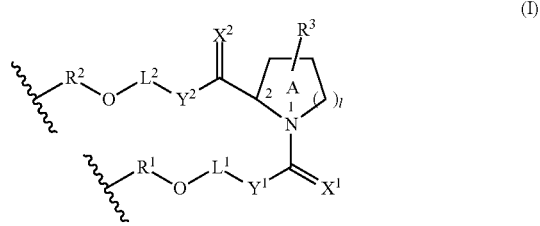

(I)

In the aforementioned formula (I), for example,
$X^1$ and $X^2$ are each independently $H_2$, O, S, or NH;
$Y^1$ and $Y^2$ are each independently a single bond, $CH_2$, NH, O, or S;
$R^3$ is a hydrogen atom or a substituent bonded to C-3, C-4, C-5 or C-6 on ring A, $L^1$ is an alkylene chain composed of n atoms, and a hydrogen atom on an alkylene carbon atom may or may not be substituted with OH, $OR^a$, $NH_2$, $NHR^a$, $NR^aR^b$, SH, or $SR^a$, or
$L^1$ is a polyether chain obtained by substituting at least one carbon atom on the aforementioned alkylene chain with an oxygen atom,
provided that: when $Y^1$ is NH, O, or S, an atom bound to $Y^1$ in $L^1$ is carbon, an atom bound to $OR^1$ in $L^1$ is carbon, and oxygen atoms are not adjacent to each other;
$L^2$ is an alkylene chain composed of m atoms, and a hydrogen atom on an alkylene carbon atom may or may not be substituted with OH, $OR^c$, $NH_2$, $NHR^c$, $NR^cR^d$, SH, or $SR^c$, or
$L^2$ is a polyether chain obtained by substituting at least one carbon atom on the aforementioned alkylene chain with an oxygen atom,
provided that: when $Y^2$ is NH, O, or S, an atom bound to $Y^2$ in $L^2$ is carbon, an atom bound to $OR^2$ in $L^2$ is carbon, and oxygen atoms are not adjacent to each other;
$R^a$, $R^b$, $R^c$, and $R^d$ are each independently a substituent or a protecting group;
l is 1 or 2;
m is an integer in the range from 0 to 30;
n is an integer in the range from 0 to 30;
in ring A, one carbon atom other than C-2 on the aforementioned ring A may be substituted by nitrogen, oxygen or sulfur,
the aforementioned ring A may contain a carbon-carbon double bond or a carbon-nitrogen double bond,
the aforementioned regions (Xc) and (X) are each linked to the aforementioned linker region (Lx) via —$OR^1$— or —$OR^2$—,
the aforementioned region (Yc) and the aforementioned region (Y) are each linked to the aforementioned linker region (Ly) via —$OR^1$— or —$OR^2$—,
wherein $R^1$ and $R^2$ may or may not be present, and when they are present, $R^1$ and $R^2$ are each independently a nucleotide residue or the aforementioned structure (I).

In the aforementioned formula (I), for example, $X^1$ and $X^2$ are each independently $H_2$, O, S, or NH. In the aforementioned formula (I), "$X^1$ is $H_2$," means that $X^1$ forms $CH_2$ (a methylene group) together with a carbon atom to which $X^1$ binds. The same applies to $X^2$.

In the aforementioned formula (I), $Y^1$ and $Y^2$ are each independently a single bond, $CH_2$, NH, O, or S.

In the aforementioned formula (I), in ring A, l is 1 or 2. When l=1, ring A is a 5-membered ring, for example, the aforementioned pyrrolidine skeleton. The aforementioned pyrrolidine skeleton is, for example, proline skeleton, prolinol skeleton or the like, and exemplified by the divalent structures thereof. When l=2, ring A is a 6-membered ring, for example, the aforementioned piperidine skeleton. In ring A, one carbon atom other than C-2 on ring A may be substituted by nitrogen, oxygen or sulfur. Ring A may contain, in ring A, a carbon-carbon double bond or a carbon-nitrogen double bond. Ring A is, for example, L type or D type.

In the aforementioned formula (I), $R^3$ is a hydrogen atom or a substituent bonded to C-3, C-4, C-5 or C-6 on ring A. When $R^3$ is the aforementioned substituent, substituent $R^3$ may be one or plural or absent and, when it is in plurality, they may be the same or different.

The substituent $R^3$ is, for example, halogen, OH, $OR^4$, $NH_2$, $NHR^4$, $NR^4R^5$, SH, $SR^4$ or an oxo group (=O) and the like.

For example, $R^4$ and $R^5$ are each independently a substituent or a protecting group, and may be the same or different. Examples of the aforementioned substituent include halogen, alkyl, alkenyl, alkynyl, haloalkyl, aryl, heteroaryl, arylalkyl, cycloalkyl, cycloalkenyl, cycloalkylalkyl, cyclyl alkyl, hydroxyalkyl, alkoxyalkyl, aminoalkyl, heterocyclylalkenyl, heterocyclylalkyl, heteroarylalkyl, silyl, silyloxyalkyl and the like. Hereinafter the same applies. The substituent $R^3$ may be among these recited substituents.

The aforementioned protecting group is a functional group that inactivates, for example, a highly-reactive functional group. Examples of the protecting group include known protecting groups. Regarding the aforementioned protecting group, for example, the description in the literature (J. F. W. McOmie, "Protecting Groups in Organic Chemistry", Plenum Press, London and New York, 1973) can be incorporated herein. The aforementioned protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), and a dimethoxytrityl group (DMTr). When $R^3$ is $OR^4$, the aforementioned protecting group is not particularly limited, and examples thereof include a TBDMS group, an ACE group, a TOM group, a CEE group, a CEM group, and a TEM group. Other examples of the protecting group include silyl-containing groups represented by the chemical formula [ka5] to be shown later. The same applies hereinafter.

In the aforementioned formula (I), $L^1$ is an alkylene chain composed of n atoms. A hydrogen atom(s) on the aforementioned alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the aforementioned alkylene chain with an oxygen atom. The aforementioned polyether chain is, for example, polyethylene glycol. When $Y^1$ is NH, O, or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the aforementioned formula (I), $L^2$ is an alkylene chain composed of m atoms. A hydrogen atom(s) on the aforementioned alkylene carbon atom(s) may or may not be substituted with, for example, OH, $OR^c$, $NH_2$, $NHR^c$, $NR^cR^d$, SH, or $SR^c$. Alternatively, $L^2$ may be a polyether chain obtained by substituting at least one carbon atom on the aforementioned alkylene chain with an oxygen atom. When $Y^2$ is NH, O, or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. For example, n and m can be set as appropriate depending on a desired length of the aforementioned linker region (Lx) or (Ly). For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

$R^a$, $R^b$, $R^c$ and $R^d$ are each independently a substituent or a protecting group. Examples of the aforementioned substituent and the aforementioned protecting group are the same as those mentioned above.

In the aforementioned formula (I), hydrogen atoms each independently may be substituted with, for example, a halogen such as Cl, Br, F, or I.

The aforementioned regions (Xc) and (X) are each linked to the aforementioned linker region (Lx) and the aforementioned regions (Yc) and (Y) are each linked to the aforementioned linker region (Ly) via, for example, $-OR^1-$ or $-OR^2-$, respectively. $R^1$ and $R^2$ may or may not be present. When $R^1$ and $R^2$ are present, $R^1$ and $R^2$ are each independently a nucleotide residue or the structure represented by the aforementioned formula (I). When $R^1$ and/or $R^2$ are/is the aforementioned nucleotide residue, the aforementioned linker region (Lx) and the aforementioned linker region (Ly) are composed of, for example, the aforementioned non-nucleotide residue having the structure of the aforementioned formula (I) excluding the nucleotide residue $R^1$ and/or $R^2$, and the aforementioned nucleotide residue(s). When $R^1$ and/or $R^2$ are/is the structure represented by the aforementioned formula (I), the structure of the aforementioned linker region (Lx) and the aforementioned linker region (Ly) are such that, for example, two or more of the aforementioned non-nucleotide residues having the structure of the aforementioned formula (I) are linked to each other. The number of the structures of the aforementioned formula (I) may be, for example, 1, 2, 3, or 4. When the linker region (Lx) or the linker region (Ly) includes a plurality of the aforementioned structures, the structures of the aforementioned (I) may be linked, for example, either directly or via the aforementioned nucleotide residue(s). On the other hand, when $R^1$ and $R^2$ are not present, the aforementioned linker region (Lx) and the aforementioned linker region (Ly) are composed of, for example, the aforementioned non-nucleotide residue having the structure of the aforementioned formula (I) alone.

The combination of the aforementioned regions (Xc) and (X) with aforementioned $-OR^1-$ and $-OR^2-$, and the combination of the aforementioned regions (Yc) and (Y) with aforementioned $-OR^1-$ and $-OR^2-$ are not particularly limited, and may be, for example, any of the following conditions:

Condition (1):
the aforementioned regions (Xc) and (X) are linked to the structure of the aforementioned formula (I) via $-OR^2-$ and $-OR^1-$, respectively; and
the aforementioned regions (Yc) and (Y) are linked to the structure of the aforementioned formula (I) via $-OR^1-$ and $-OR^2-$, respectively.

Condition (2):
the aforementioned regions (Xc) and (X) are linked to the structure of the aforementioned formula (I) via $-OR^2-$ and $-OR^1-$, respectively; and
the aforementioned regions (Yc) and (Y) are linked to the structure of the aforementioned formula (I) via $-OR^2-$ and $-OR^1-$, respectively.

Condition (3):
the aforementioned regions (Xc) and (X) are linked to the structure of the aforementioned formula (I) via $-OR^1-$ and $-OR^2-$, respectively; and the aforementioned regions (Yc) and (Y) are linked to the structure of the aforementioned formula (I) via —OR$^1$— and —OR$^2$—, respectively.

Condition (4):

the aforementioned regions (Xc) and (X) are linked to the structure of the aforementioned formula (I) via —OR$^1$— and —OR$^2$—, respectively; and the aforementioned regions (Yc) and (Y) are linked to the structure of the aforementioned formula (I) via —OR$^2$— and —OR$^1$—, respectively.

Examples of the structure of the aforementioned formula (I) include the structures of the following formulae (I-1) to (I-9). In the following formulae, n and m are the same as in the aforementioned formula (I). In the following formulae, q is an integer of 0-10.

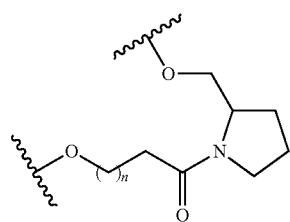
(1-1)

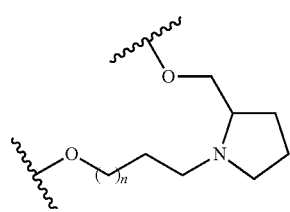
(1-2)

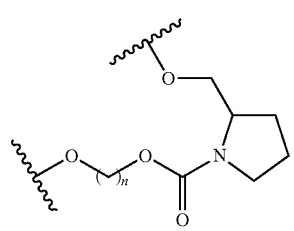
(1-3)

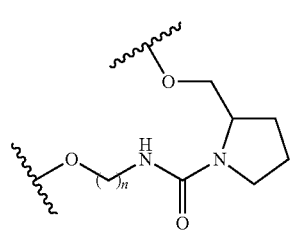
(1-4)

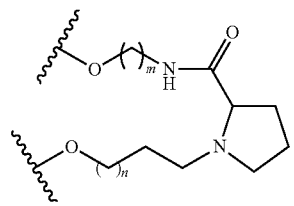
(1-5)

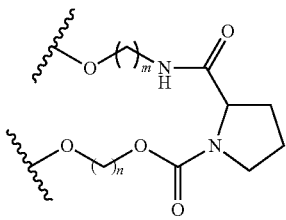
(1-6)

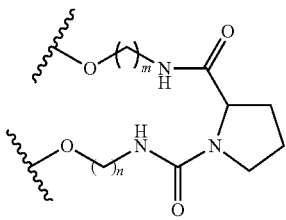
(1-7)

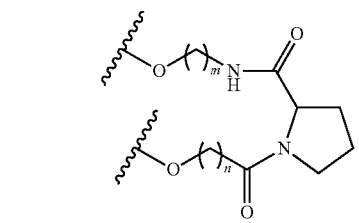
(1-8)

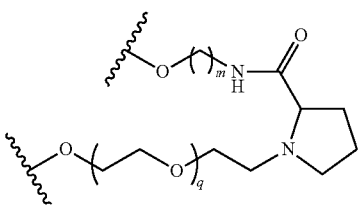
(1-9)

In the aforementioned formulae (I-1) to (I-9), n, m and q are not particularly limited, and are as described above. Specific examples thereof include the aforementioned formula (I-1) wherein n=8, the aforementioned (I-2) wherein n=3, the aforementioned formula (I-3) wherein n=4 or 8, the aforementioned (I-4) wherein n=7 or 8, the aforementioned formula (I-5) wherein n=3 and m=4, the aforementioned (I-6) wherein n=8 and m=4, the aforementioned formula (I-7) wherein n=8 and m=4, the aforementioned (I-8) wherein n=5 and m=4, and the aforementioned formula (I-9) wherein q=1 and m=4. One embodiment (n=8) of the aforementioned formula (I-4) is shown in the following formula (I-4a), and one embodiment (n=5, m=4) of the aforementioned formula (I-6) is shown in the following formula (I-6a).

A preferable embodiment of the nucleic acid molecule of the present invention in the first form wherein the linker region Lx is a structure shown by the following formula (I-6a) is, for example, a nucleic acid molecule consisting of (a) the base sequence shown in SEQ ID NO: 5, the structure shown by the following formula (I-6a), and the base sequence shown in SEQ ID NO: 13, or (b) the base sequence shown in SEQ ID NO: 6, the structure shown by the following formula (I-6a), and the base sequence shown in SEQ ID NO: 14. A preferable embodiment of the nucleic acid molecule of the present invention in the second form wherein the linker regions Lx and Ly are a structure shown by the following formula (I-6a) is, for example, a nucleic acid molecule consisting of (a) the base sequence shown in SEQ ID NO: 11, the structure shown by the following formula (I-6*a*), the base sequence shown in SEQ ID NO: 15, the structure shown by the following formula (I-6a), and G, or (b) the base sequence shown in SEQ ID NO: 12, the structure shown by the following formula (I-6a), the base sequence shown in SEQ ID NO: 16, the structure shown by the following formula (I-6a), and G.

```
PHR-0001
5'-UGGAAACCCACAACGAAAUCUCC(SEQ ID NO: 5)-
Lx-GGAGAUUUCGUUGUGGGUUUCCACC (SEQ ID NO: 13)-3'

PHR-0002
5'-UGUGACAGCAGGGAUAACACACC (SEQ ID NO: 6)-
Lx-GGUGUGUUAUCCCUGCUGUCACAGG (SEQ ID NO: 14)-3'

PKR-0001
5'-GUGGAAACCCACAACGAAAUCUCC (SEQ ID NO: 11)-
Lx-GGAGAUUUCGUUGUGGGUUUCCACCC (SEQ ID NO: 15)-
Ly-G-3'

PKR-0002
5'-CUGUGACAGCAGGGAUAACACACC (SEQ ID NO: 12)-
Lx-GGUGUGUUAUCCCUGCUGUCACAGGC (SEQ ID NO: 16)-
Ly-G-3'
```

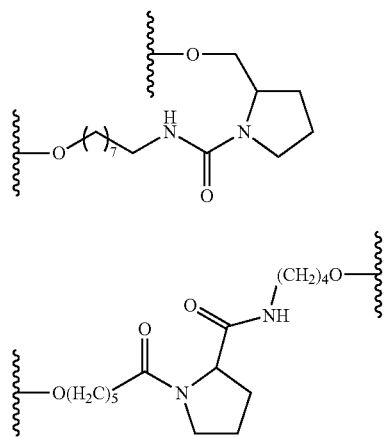

The constitutional units of the the nucleic acid molecule of the present invention are not particularly limited and nucleotide residues can be mentioned. Examples of the aforementioned nucleotide residues include a ribonucleotide residue and a deoxyribonucleotide residue. The aforementioned nucleotide residue may be, for example, the one that is not modified (unmodified nucleotide residue) or the one that has been modified (modified nucleotide residue). By configuring the nucleic acid molecule of the present invention to include the aforementioned modified nucleotide residue, for example, the resistance of the molecule to nuclease can be improved, thereby allowing the stability of the nucleic acid molecule to be improved. Furthermore, the nucleic acid molecule of the present invention further may include, for example, a non-nucleotide residue in addition to the aforementioned nucleotide residue.

In the nucleic acid molecule of the present invention, the constitutional unit of each of the aforementioned linker other than region is preferably the aforementioned nucleotide residue. Each of the aforementioned regions is composed of, for example, any of the following residues (1) to (3):
(1) an unmodified nucleotide residue(s)
(2) a modified nucleotide residue(s)
(3) an unmodified nucleotide residue(s) and a modified nucleotide residue(s).

In the nucleic acid molecule of the present invention, the constitutional unit of the aforementioned linker region is not particularly limited, and examples thereof include the aforementioned nucleotide residues and the aforementioned non-nucleotide residues. Each of the aforementioned linker regions may be composed of, for example, the aforementioned nucleotide residue(s) only, the aforementioned non-nucleotide residue(s) only, or both the aforementioned nucleotide residue(s) and the aforementioned non-nucleotide residue(s). Each of the aforementioned linker regions is composed of, for example, any of the following residues (1) to (7):
(1) an unmodified nucleotide residue(s)
(2) a modified nucleotide residue(s)
(3) an unmodified nucleotide residue(s) and a modified nucleotide residue(s)
(4) a non-nucleotide residue(s)
(5) a non-nucleotide residue(s) and an unmodified nucleotide residue(s)
(6) a non-nucleotide residue(s) and a modified nucleotide residue(s)
(7) a non-nucleotide residue(s), an unmodified nucleotide residue(s), and a modified nucleotide residue(s).

When the nucleic acid molecule of the present invention has both the aforementioned linker region (Lx) and the aforementioned linker region (Ly), for example, the constitution units of the both may be the same or different. Specific examples thereof include a form wherein the constitution units of the both linker regions are the aforementioned nucleotide residues, a form wherein the constitution units of the both linker regions are the aforementioned non-nucleotide residues, one of the constitution units of the region is the aforementioned nucleotide residue, and the constitution unit of the other linker region is a non-nucleotide residue and the like.

Examples of the nucleic acid molecule of the present invention include molecules composed of the aforementioned nucleotide residues only; and molecules including the aforementioned non-nucleotide residue(s) in addition to the aforementioned nucleotide residues. In the nucleic acid molecule of the present invention, for example, the aforementioned nucleotide residues may be the aforementioned unmodified nucleotide residues only; the aforementioned modified nucleotide residues only; or both the aforementioned unmodified nucleotide residue(s) and the aforementioned modified nucleotide residue(s), as described above. When the aforementioned nucleic acid molecule includes both the aforementioned unmodified nucleotide residue(s) and the aforementioned modified nucleotide residue(s), the number of the aforementioned modified nucleotide residue(s) is not particularly limited, and is, for example, "one to several", specifically, for example, 1 to 5, preferably 1 to 4, more preferably 1 to 3, and most preferably 1 or 2. When the nucleic acid molecule of the present invention include the aforementioned non-nucleotide residue(s), the number of the aforementioned non-nucleotide residue(s) is not particularly limited, and is, for example, "one to several", specifically, for example, 1-8, 1-6, 1-4, 1, 2 or 3.

When the aforementioned nucleic acid molecule includes, for example, the aforementioned modified ribonucleotide residue(s) in addition to the aforementioned unmodified ribonucleotide residues, the number of the aforementioned modified ribonucleotide residue(s) is not particularly limited, and is, for example, "one to several", specifically, for example, 1 to 5, preferably 1 to 4, more preferably 1 to 3, and most preferably 1 or 2. The aforementioned modified ribonucleotide residue as contrasted to the aforementioned unmodified ribonucleotide residue may be, for example, the aforementioned deoxyribonucleotide residue obtained by substituting a ribose residue with a deoxyribose residue. When the aforementioned nucleic acid molecule includes, for example, the aforementioned deoxyribonucleotide residue(s) in addition to the aforementioned unmodified ribonucleotide residue(s), the number of the aforementioned deoxyribonucleotide residue(s) is not particularly limited, and is, for example, "one to several", specifically, for example, 1 to 5, preferably 1 to 4, more preferably 1 to 3, and most preferably 1 or 2.

The nucleic acid molecule of the present invention may include, for example, a labeling substance, and may be labeled with the aforementioned labeling substance. The aforementioned labeling substance is not particularly limited, and may be, for example, a fluorescent substance, a dye, an isotope, or the like. Examples of the aforementioned labeling substance include: fluorophores such as pyrene, TAMRA, fluorescein, a Cy3 dye, and a Cy5 dye. Examples of the aforementioned dye include Alexa dyes such as Alexa 488. Examples of the aforementioned isotope include stable isotopes and radioisotopes. Among them, stable isotopes are preferable. For example, the aforementioned stable isotopes have a low risk of radiation exposure and they require no dedicated facilities. Thus, stable isotopes are excellent in handleability and can contribute to cost reduction. Moreover, for example, the aforementioned stable isotope does not change the physical properties of a compound labeled therewith and thus has an excellent property as a tracer. The aforementioned stable isotope is not particularly limited, and examples thereof include $^{2}H$, $^{13}C$, $^{15}N$, $^{17}O$, $^{18}O$, $^{33}S$, $^{34}S$, and, $^{36}S$.

The nucleic acid molecule of the present invention can inhibit the expression of a TGF-β1 gene, as mentioned above. Thus, the nucleic acid molecule of the present invention can be used, for example, as a therapeutic agent for treating a disease caused by a TGF-β1 gene. In the present invention, the term "treatment" encompasses: prevention of the aforementioned diseases; improvement of the diseases; and improvement in prognosis, for example, and it can mean any of them. As the aforementioned disease, acute lung injury; interstitial pneumonia/pulmonary fibrosis; COPD (chronic obstructive pulmonary disease); bronchial asthma and the like can be mentioned.

The method of using the nucleic acid molecule of the present invention is not particularly limited. For example, the aforementioned nucleic acid molecule may be administered to a subject having the aforementioned TGF-β1 gene.

Examples of the aforementioned subject to which the nucleic acid molecule of the present invention is administered include cells, tissues and organs. Examples of the aforementioned subject also include humans, human animals such as nonhuman mammals, i.e., mammals excluding humans. The aforementioned administration may be performed, for example, in vivo or in vitro. The aforementioned cells are not particularly limited, and examples thereof include: various cultured cells such as A549, HeLa, 293, COS7 and the like; pluripotent stem cells such as ES cell, iPS cell and the like, somatic stem cells such as hematopoietic stem cell and the like, various cultured cells induced to differentiate from the aforementioned pluripotent stem cell or somatic stem cell; and cells isolated from living organisms, such as primary cultured cell and the like.

As to the use of the nucleic acid molecule of the present invention, the following description regarding the composition, the expression inhibitory method, the treatment method, and the like according to the present invention to be describe below can be referred to.

Since the nucleic acid molecule of the present invention can inhibit the expression of TGF-β1 gene as described above, for example, it is useful as a pharmaceutical product, a diagnostic agent, an agricultural chemical, and a tool for conducting research on agricultural chemical, medical science, life science, and the like.

2. Nucleotide Residue

The aforementioned nucleotide residue includes, for example, a sugar, a base, and a phosphate as its components. The aforementioned nucleotide residue may be, for example, a ribonucleotide residue or a deoxyribonucleotide residue, as described above. The aforementioned ribonucleotide residue has, for example, a ribose residue as the sugar; and adenine (A), guanine (G), cytosine (C), or uracil (U) as the base. The aforementioned deoxyribose residue has, for example, a deoxyribose residue as the sugar; and adenine (A), guanine (G), cytosine (C), or thymine (T) as the base.

The aforementioned nucleotide residue may be, for example, an unmodified nucleotide residue or a modified nucleotide residue. The aforementioned components of the aforementioned unmodified nucleotide residue are the same or substantially the same as, for example, the components of a naturally-occurring nucleotide residue. Preferably, the components are the same or substantially the same as the components of a nucleotide residue occurring naturally in a human body.

The aforementioned modified nucleotide residue is, for example, a nucleotide residue obtained by modifying the aforementioned unmodified nucleotide residue. For example, the aforementioned modified nucleotide residue may be such that any of the components of the aforementioned unmodified nucleotide residue is modified. In the present invention, "modification" means, for example, substitution, addition, and/or deletion of any of the aforementioned components; and substitution, addition, and/or deletion of an atom(s) and/or a functional group(s) in the aforementioned component(s). It can also be referred to as "modification". Examples of the aforementioned modified nucleotide residue include naturally-occurring nucleotide residues and artificially-modified nucleotide residues. Regarding the aforementioned naturally-derived modified nucleotide residues, for example, Limbach et al. (Limbach et al., 1994, Summary: the modified nucleosides of RNA, Nucleic Acids Res. 22: pp. 2183 to 2196) can be referred to. The aforementioned modified nucleotide residue may be, for example, a residue of an alternative of the aforementioned nucleotide.

Examples of the modification of the aforementioned nucleotide residue include modification of a ribose-phosphate backbone (hereinafter referred to as a "ribophosphate backbone").

In the aforementioned ribophosphate backbone, for example, a ribose residue may be modified. In the aforementioned ribose residue, for example, the 2'-position carbon can be modified. Specifically, a hydroxyl group bound to, for example, the 2'-position carbon can be substituted with hydrogen or halogen such as fluoro. By substituting the hydroxyl group bound to the aforementioned 2'-position carbon with hydrogen, it is possible to substitute the ribose residue with deoxyribose. The aforementioned ribose residue can be substituted with its stereoisomer, for example, and may be substituted with, for example, an arabinose residue.

The aforementioned ribophosphate backbone may be substituted with, for example, a non-ribophosphate backbone having a non-ribose residue and/or a non-phosphate. The aforementioned non-ribophosphate backbone may be, for example, the aforementioned ribophosphate backbone modified to be uncharged. Examples of an alternative obtained by substituting the ribophosphate backbone with the aforementioned non-ribophosphate backbone in the aforementioned nucleotide include morpholino, cyclobutyl, and pyrrolidine. Other examples of the aforementioned alternative include artificial nucleic acid monomer residues. Specific examples thereof include PNA (Peptide Nucleic Acid), LNA (Locked Nucleic Acid), and ENA (2'-O,4'-C-Ethylenebridged Nucleic Acid). Among them, PNA is preferable.

In the aforementioned ribophosphate backbone, for example, a phosphate group can be modified. In the aforementioned ribophosphate backbone, a phosphate group at the closest adjacency to the sugar residue is called an "α-phosphate group". The aforementioned α-phosphate group is charged negatively, and the electric charges are distributed evenly over two oxygen atoms that are not linked to the sugar residue. Among the four oxygen atoms in the aforementioned α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the aforementioned nucleotide residues hereinafter are referred to as "linking oxygens". For example, the aforementioned α-phosphate group is preferably modified to be uncharged, or to render the charge distribution between the aforementioned non-linking oxygen asymmetric.

In the aforementioned phosphate group, for example, the aforementioned non-linking oxygen(s) may be substituted. The aforementioned oxygen(s) can be substituted with, for example, any atom selected from S (sulfur), Se (selenium), B (boron), C (carbon), H (hydrogen), N (nitrogen), and OR (R is, for example, an alkyl group or an aryl group) and substitution with S is preferable. It is preferable that both the aforementioned non-linking oxygens are substituted, for example, and it is more preferable that both the non-linking oxygens are substituted with S. Examples of the aforementioned modified phosphate group include phosphorothioates, phosphorodithioates, phosphoroselenates, boranophosphates, boranophosphates, hydrogen phosphonates, phosphoroamidates, alkyl or aryl phosphonates, and phosphotriesters. In particular, phosphorodithioate in which both of the aforementioned two non-linking oxygens are substituted with S is preferable.

In the aforementioned phosphate group, for example, the aforementioned linking oxygen(s) may be substituted. The aforementioned oxygen(s) can be substituted with, for example, any atom selected from S (sulfur), C (carbon), and N (nitrogen). Examples of the aforementioned modified phosphate group include: bridged phosphoroamidates resulting from the substitution with N; bridged phosphorothioates resulting from the substitution S; and bridged methylenephosphonates resulting from the substitution C. Preferably, substitution of the aforementioned linking oxygen(s) is performed in, for example, at least one of the 5'-terminus nucleotide residue and the 3'-terminus nucleotide residue of the nucleic acid molecule of the present invention. When the substitution is performed on the 5'-side, substitution with C is preferable. When the substitution is performed on the 3'-side, substitution with N is preferable.

The aforementioned phosphate group may be substituted with, for example, the aforementioned phosphate-free linker. The aforementioned linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylenecarbonylamino group and a methylenemethylimino group.

In the nucleic acid molecule of the present invention, for example, at least one of a nucleotide residue at the 3'-terminus and a nucleotide residue at the 5'-terminus may be modified. For example, the nucleotide residue at either one of the 3'-terminus and the 5'-terminus may be modified, or the nucleotide residues at both the 3'-terminus and the 5'-terminus may be modified. The aforementioned modification may be, for example, as described above, and it is preferable to modify a phosphate group(s) at the end(s). For example, the entire aforementioned phosphate group may be modified, or one or more atoms in the aforementioned phosphate group may be modified. In the former case, for example, the entire phosphate group may be substituted or deleted.

Modification of the aforementioned nucleotide residue(s) at the end(s) may be, for example, addition of any other molecule. Examples of the aforementioned other molecule include functional molecules such as labeling substances as described above and protecting groups. Examples of the aforementioned protecting groups include S (sulfur), Si (silicon), B (boron), and ester-containing groups. The functional molecules such as the aforementioned labeling substances can be used, for example, in the detection and the like of the nucleic acid molecule of the present invention.

The aforementioned other molecule may be, for example, added to the phosphate group of the aforementioned nucleotide residue or may be added to the aforementioned phosphate group or the aforementioned sugar residue via a spacer. For example, the terminus atom of the aforementioned spacer can be added to or substituted for either one of the aforementioned linking oxygens of the aforementioned phosphate group, or O, N, S, or C of the sugar residue. The binding site in the aforementioned sugar residue preferably is, for example, C at the 3'-position, C at the 5'-position, or any atom bound thereto. For example, the aforementioned spacer can also be added to or substituted for a terminus atom of the aforementioned nucleotide alternative such as PNA.

The aforementioned spacer is not particularly limited, and examples thereof include $-(CH_2)_n-$, $-(CH_2)_nN-$, $-(CH_2)_nO-$, $-(CH_2)_nS-$, $O(CH_2CH_2O)_nCH_2CH_2OH$, abasic sugars, amide, carboxy, amine, oxyamine, oxyimine, thioether, disulfide, thiourea, sulfonamide, and morpholino, and also biotin reagents and fluorescein reagents. In the aforementioned formulae, n is a positive integer, and n=3 or 6 is preferable.

Other examples of the aforementioned molecule to be added to the end include dyes, intercalating agents (e.g., acridines), crosslinking agents (e.g., psoralen, mitomycin C), porphyrins (TPPC4, texaphyrin, sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrenebutyric acid, dihydrotestosterone, 1,3-Bis-O (hexadecyl)glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl)cholic acid, dimethoxytrityl, or phenoxathiine), peptide complexes (e.g., Antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), and synthetic ribonucleases (e.g., imidazole, bisimidazole, histamine, imidazole clusters, acridine-imidazole complexes, Eu$^{3+}$ complexes of tetraazamacrocycles).

In the nucleic acid molecule of the present invention, the aforementioned 5'-terminus may be, for example, modified by a phosphoric acid group or a phosphoric acid group analog. Examples of the aforementioned phosphoric acid group include 5'-monophosphate ((HO)$_2$(O)P—O-5'); 5'-diphosphate ((HO)$_2$(O) P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated, 7m-G-O-5'-(HO)(O)P—O—(HO)(O)P—O—P(HO)(O)—O-5'); 5'-adenosine cap (Appp); any modified or unmodified nucleotide cap structure (N—O-5'-(HO)(O)P—O—(HO)(O)P—O—P(HO)(O)—O-5'); 5'-monothiophosphate (phosphorothioate: (HO)$_2$(S)P—O-5'); 5'-monodithiophosphate (phosphorodithioate: (HO)(HS)(S)P—O-5'); 5'-phosphorothiolate ((HO)$_2$(O) P—S-5'); sulfur substituted monophosphate, diphosphate, and triphosphates (e.g., 5'-α-thiotriphosphate, 5'-γ-thiotriphosphate, and the like); 5'-phosphoramidates ((HO)$_2$(O) P—NH-5' (HO)(NH$_2$)(O) P—O-5'); 5'-alkylphosphonates (e.g., RP(OH)(O)—O-5', (OH)$_2$(O)P-5'-CH$_2$, where R is alkyl (e.g., methyl, ethyl, isopropyl, propyl, or the like)); and 5'-alkyletherphosphonates (e.g., RP(OH)(O)—O-5', where R is alkylether (e.g., methoxymethyl, ethoxymethyl, or the like)).

In the aforementioned nucleotide residue, the aforementioned base is not particularly limited. The aforementioned base may be, for example, a natural base or a non-natural base. The aforementioned base may be, for example, a naturally-derived base or a synthetic base. As the aforementioned base, for example, a common base, a modified analog thereof, and the like can be used.

Examples of the aforementioned base include: purine bases such as adenine and guanine; and pyrimidine bases such as cytosine, uracil, and thymine. Other examples of the aforementioned base include inosine, thymine, xanthine, hypoxanthine, nubularine, isoguanisine, and tubercidine. Examples of the aforementioned base also include: 2-amino-adenine, alkyl derivatives such as 6-methylated purine; alkyl derivatives such as 2-propylated purine; 5-halouracil and 5-halocytosine; 5-propynyluracil and 5-propynylcytosine; 6-azouracil, 6-azocytosine, and 6-azothymine; 5-uracil (pseudouracil), 4-thiouracil, 5-halouracil, 5-(2-aminopropyl)uracil, 5-aminoallyluracil; 8-halogenated, aminated, thiolated, thioalkylated, hydroxylated, and other 8-substituted purines; 5-trifluoromethylated and other 5-substituted pyrimidines; 7-methylguanine; 5-substituted pyrimidines; 6-azapyrimidines; N-2, N-6, and O-6 substituted purines (including 2-aminopropyladenine); 5-propynyluracil and 5-propynylcytosine; dihydrouracil; 3-deaza-5-azacytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazoles; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N4-acetylcytosine; 2-thiocytosine; N6-methyladenine; N6-isopentyladenine; 2-methylthio-N6-isopentyladenine; N-methylguanine; and O-alkylated bases. Examples of the purines and pyrimidines include those disclosed in U.S. Pat. No. 3,687,808, "Concise Encyclopedia of Polymer Science and Engineering", pp. 858 to 859, edited by Kroschwitz J. I, John Wiley & Sons, 1990, and Englisch et al, Angewandte Chemie, International Edition, 1991, vol. 30, p. 613.

Other examples of the aforementioned modified nucleotide residue include those having no base, i.e., those having an abasic ribophosphate backbone. Furthermore, as the aforementioned modified nucleotide residue, for example, those described in U.S. Provisional Application No. 60/465,665 (filing date: Apr. 25, 2003) and International Application No. PCT/US04/07070 (filing date: Mar. 8, 2004) can be used and these documents are incorporated herein by reference.

3. Synthesis Method of Nucleic Acid Molecule of the Present Invention

The method for synthesizing the nucleic acid molecule of the present invention is not particularly limited, and a conventionally known method can be employed. Examples of the aforementioned synthesis method include synthesis methods according to genetic engineering procedures and chemical synthesis methods. Examples of the genetic engineering procedures include: synthesis methods utilizing in vitro transcription; methods using a vector; methods carried out using a PCR cassette and the like. The aforementioned vector is not particularly limited, and examples thereof include non-virus vectors such as plasmid, and virus vectors. The aforementioned chemical synthesis methods are not particularly limited, and examples thereof include a phosphoramidite method and an H-phosphonate method. The aforementioned chemical synthesis methods can be carried out, for example, using a commercially available automated nucleic acid synthesizer. In the aforementioned chemical synthesis methods, an amidite is generally used. The aforementioned amidite is not particularly limited. Examples of commercially available amidites include RNA Phosphoramidites (2'-O-TBDMSi, trade name, Samchully Pharm. Co., Ltd.), ACE amidite and TOM amidite, CEE amidite, CEM amidite, and TEM amidite and the like.

4. Expression Vector

The expression vector according to the present invention characteristically contains DNA encoding the aforementioned nucleic acid molecule of the present invention. The expression vector of the present invention is characterized in that it contains the aforementioned DNA, and other configurations are by no means limited. In the expression vector of the present invention, for example, DNA is inserted so that it can be expressed in the vector. The vector to be inserted with the aforementioned DNA is not particularly limited and, for example, general vectors can be used such as virus vector, non-virus vector and the like. The aforementioned non-virus vector is, for example, plasmid vector.

5. TGF-β1 Expression Inhibitor and Medicament

The expression inhibitor (or expression inhibitory composition) according to the present invention is, as described above, a preparation (or composition) for inhibiting the expression of TGF-β1 gene, and characterized in that it contains the aforementioned nucleic acid molecule of the present invention. The expression inhibitor (or expression inhibitory composition) of the present invention is characterized in that it contains the aforementioned nucleic acid molecule of the present invention, and other configurations are by no means limited. That is, the nucleic acid molecule alone may be used or an acceptable additive may be further contained according to the use object. The expression inhibitor of the present invention (or expression inhibitory composition) can also be referred to, for example, as an expression inhibitory reagent.

According to the present invention, for example, by administering to a subject in which the aforementioned TGF-β1 gene is present, it is possible to inhibit the expression of the aforementioned TGF-β1 gene.

Furthermore, as described above, the medicament (or the pharmaceutical composition) according to the present invention characteristically contains the aforementioned nucleic acid molecule of the present invention. The medicament (or the composition of the present invention) is characterized in that it contains the aforementioned nucleic acid molecule of the present invention, and other configurations are by no means limited. That is, the nucleic acid molecule alone may be used or a pharmaceutically acceptable additive may be further contained.

According to the present invention, for example, administration to a patient with a disease caused by the aforementioned TGF-β1 gene can inhibit the expression of the gene, thereby treating the aforementioned disease. The aforementioned disease is, for example, as described above, and acute lung injury, interstitial pneumonia/pulmonary fibrosis and the like can be mentioned. In the present invention, the term "treatment" encompasses, as mentioned above, prevention of the aforementioned diseases; improvement of the diseases; and improvement in prognosis, for example, and it can mean any of them.

The method of using the expression inhibitor (or expression inhibitory composition) and the medicament (or the pharmaceutical composition) according to the present invention (hereinafter to be referred to as "the agent/composition of the present invention") is not particularly limited, and examples thereof include administering the aforementioned nucleic acid molecule to a subject having the aforementioned TGF-β1 gene.

Examples of the aforementioned subject to which the nucleic acid molecule of the present invention is administered include cells, tissues and organs. Examples of the aforementioned subject also include humans, nonhuman animals such as nonhuman mammals, i.e., mammals excluding humans. The aforementioned administration may be performed, for example, in vivo or in vitro. The aforementioned cells are not particularly limited, and examples thereof include the aforementioned cells and the like.

The aforementioned administration method is not particularly limited, and can be determined, for example, as appropriate depending on the subject. When the aforementioned subject is a cultured cell, the administration method may be, for example, a method using a transfection reagent, an electroporation method, or the like.

For example, the agent/composition of the present invention may contain, as mentioned above, only the nucleic acid molecule of the present invention or further may contain an additive(s) in addition to the nucleic acid molecule. The aforementioned additive is not particularly limited, and is preferably, for example, a pharmaceutically acceptable additive. The kind of the aforementioned additive is not particularly limited, and can be selected as appropriate depending on, for example, the kind of the subject.

In the composition of the present invention, for example, the aforementioned nucleic acid molecule may form a complex with the aforementioned additive. The aforementioned additive can also be referred to, for example, as a complexing agent. The aforementioned complex formation allows, for example, the aforementioned nucleic acid molecule to be delivered efficiently. The bond between the aforementioned nucleic acid molecule and the aforementioned complexing agent is not particularly limited, and examples thereof include noncovalent bond. The aforementioned complex may be, for example, an inclusion complex.

The aforementioned complexing agent is not particularly limited, and examples thereof include polymers, cyclodextrins, and adamantine. Examples of the aforementioned cyclodextrins include linear cyclodextrin copolymers and linear oxidized cyclodextrin copolymers.

Other examples of the aforementioned additive include a carrier, a binding substance that binds to a target cell, a condensing agent, a fusogenic agent, an excipient and the like.

6. Expression Inhibitory Method

As described above, the expression inhibitory method according to the present invention is a method for inhibiting the expression of TGF-β1 gene, which characteristically uses the aforementioned nucleic acid molecule of the present invention. The expression inhibitory method of the present invention is characterized in that the aforementioned nucleic acid molecule of the present invention is used therein, and other steps and conditions are by no means limited.

The expression inhibitory method of the present invention includes, for example, the step of administering the aforementioned nucleic acid molecule to a subject in which the aforementioned TGF-β1 gene is present. By the aforementioned administration step, for example, the aforementioned nucleic acid molecule is bought into contact with the aforementioned subject to which the nucleic acid molecule is administered. Examples of the aforementioned subject to which the nucleic acid molecule of the present invention is administered include cells, tissues and organs. Examples of the aforementioned subject also include humans, nonhuman animals such as nonhuman mammals, i.e., mammals excluding humans. The aforementioned administration may be performed, for example, in vivo or in vitro.

In the expression inhibitory method of the present invention, for example, the aforementioned nucleic acid molecule may be administered alone, or the aforementioned composition of the present invention containing the aforementioned nucleic acid molecule may be administered. The aforementioned administration method is not particularly limited and, for example, can be selected as appropriate depending on the kind of the subject.

7. Treatment Method

As described above, the method for treating a disease according to the present invention is characterized in that it includes the step of administering the aforementioned nucleic acid molecule of the present invention to a patient. The treatment method of the present invention is characterized in that the aforementioned nucleic acid molecule of the present invention is used therein, and other steps and conditions are by no means limited. The disease to be the target in the present invention is, for example, as described above, and acute lung injury, interstitial pneumonia/pulmonary fibrosis and the like can be mentioned.

The aforementioned expression inhibitory method and the like of the present invention also apply to, for example, the treatment method of the present invention. The aforementioned administration method is not particularly limited and, for example, any of oral administration and parenteral administration.

The dose of the nucleic acid molecule of the present invention in the treatment method of the present invention is not particularly limited as long as it is a therapeutically effective amount for the aforementioned disease, and varies depending on the kind and severity of the disease, animal species, age, body weight, drug tolerability of the subject of administration, administration route and the like. It may be generally about 0.0001-about 100 mg/kg, for example, about 0.001-about 10 mg/kg, preferably about 0.005-about 5 mg/kg, per dose for an adult. This amount can be administered, for example, 3 times per day—once per 2 weeks, preferably once per one day—one week.

8. Use of Nucleic Acid Molecule

The use according to the present invention is the use of the aforementioned nucleic acid molecule of the present invention for the aforementioned inhibition of the expression of TGF-β1 gene.

The present invention also provides the nucleic acid molecule of the present invention for use in inhibiting the expression of TGF-β1 gene, or in the treatment of pulmonary fibrosis or acute lung injury.

The present invention also provides a TGF-β1 gene expression inhibitor, or use of the nucleic acid molecule of the present invention in the production of a therapeutic agent for pulmonary fibrosis or acute lung injury.

In the following, the present invention will be described in detail with reference to examples and the like. It is to be noted, however, the present invention is by no means limited thereto.

EXAMPLES

Example 1

Inhibitory Effect on TGF-β1 Gene Expression of Single-Stranded Nucleic Acid Molecule in A549 Cell (1) Synthesis of Single-Stranded Nucleic Acid Molecule Single-stranded nucleic acid molecules shown below were synthesized based on the phosphoramidite method by ABI3900 nucleic acid synthesizer (trade name, Applied Biosystems). In the aforementioned synthesis, EMM amidite (WO 2013/027843) was used as RNA amidite (hereinafter the same). The aforementioned amidite was deprotected by a conventional method. The synthesized single-stranded nucleic acid molecules were purified by HPLC and respectively freeze-dried.

As single-stranded nucleic acid molecules, PHR-0001 and PKR-0001 having an expression inhibitory sequence shown in the aforementioned SEQ ID NO: 1, and PHR-0002 and PKR-0002 having an expression inhibitory sequence shown in the aforementioned SEQ ID NO: 2 were each synthesized as mentioned above. Lx in PHR-0001 and PHR-0002, and Lx and Ly in PKR-0001 and PKR-0002 are each a linker region, and the following structural formulae were obtained using L-proline diamide amidite. In each sequence, the underlined is a human TGF-β1 gene expression inhibitory sequence.

```
PHR-0001
5'-UGGAAACCCACAACGAAAUCUCC (SEQ ID NO: 5)-Lx-
GGAGAUUUCGUUGUGGGUUUCCACC (SEQ ID NO: 13)-3'

PHR-0002
5'-UGUGACAGCAGGGAUAACACACC (SEQ ID NO: 6)-Lx-
GGUGUGUUAUCCCUGCUGUCACAGG (SEQ ID NO: 14)-3'

PKR-0001
5'-GUGGAAACCCACAACGAAAUCUCC (SEQ ID NO: 11)-Lx-
GGAGAUUUCGUUGUGGGUUUCCACCC (SEQ ID NO: 15)-Ly-
G-3'

PKR-0002
5'-CUGUGACAGCAGGGAUAACACACC (SEQ ID NO: 12)-Lx-
GGUGUGUUAUCCCUGCUGUCACAGGC (SEQ ID NO: 16)-Ly-
G-3'
```

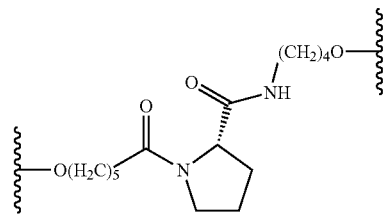

(2) Measurement of TGF-β1 Gene Expression Level

The aforementioned each single-stranded nucleic acid molecule was dissolved in distilled water for injection (Otsuka Pharmaceutical Co., Ltd.) to 20 μmol/L.

As the cells, A549 cells (DS Pharma Biomedical Co., Ltd.) was used. As a medium, DMEM containing 10% FBS (Invitrogen) was used. The culture conditions were 37° C., 5% $CO_2$.

The cells were first seeded in a 24-well plate at $4 \times 10^4$ cells/400 μL medium/well. Thereafter, the cells were transfected with the aforementioned single-stranded nucleic acid molecule by using (A) transfection reagent Lipofectamine RNAiMAX (Invitrogen) according to the protocol attached to the aforementioned transfection reagent. Specifically, the transfection was carried out by setting the composition per well as follows. In the following compositions, (B) is Opti-MEM (Invitrogen), (C) is 20 μmol/L single-stranded nucleic acid molecule solution mentioned above, and 98.5 μL of a total of the both was added. The final concentration of the aforementioned single-stranded nucleic acid molecule in the aforementioned well was set to 0.1, 1 nmol/L.

TABLE 1

| (composition per well: μL) | |
|---|---|
| culture solution | 400 |
| transfection reagent | 1.5 |
| (B) + (C) | 98.5 |
| total | 500 |

After the transfection, the cells in the aforementioned wells were cultured for 24 hours, and then, the RNA was collected using an RNeasy Mini Kit (Qiagen) according to the protocol supplied therewith. Subsequently, cDNA was synthesized from the aforementioned RNA using Transcription First Strand cDNA Synthesis Kit (Roche) according to the protocol supplied therewith. Then, as shown below, PCR was carried out using the aforementioned synthesized cDNA as a template, and the expression level of the TGF-β1 gene and that of the β-actin gene as an internal standard were measured. The aforementioned expression level of the TGF-β1 gene was normalized with reference to that of the β-actin gene mentioned above.

The aforementioned PCR was carried out using LightCycler 480 SYBR Green I Master (Roche) as a reagent and LightCycler 480 (Roche) as an instrument (hereinafter the same). The aforementioned TGF-β1 gene and β-actin gene were amplified using the following primer sets, respectively.

PCR Primer Set for TGF-β1 Gene

```
                                    (SEQ ID NO: 7)
  5'-TTGTGCGGCAGTGGTTGAGCCG-3'

(SEQ ID NO: 8)
  5'-GAAGCAGGAAAGGCCGGTTCATGC-3' primer set for β-actin gene
                                    (SEQ ID NO: 9)
  5'-GCCACGGCTGCTTCCAGCTCCTC-3'

(SEQ ID NO: 10)
  5'-AGGTCTTTGCGGATGTCCACGTCAC-3'
```

As control 1, regarding the cells to which the aforementioned culture solution and 100 μL of the aforementioned solution (B) only had been added, the expression levels of the genes also were measured (−). Furthermore, as control 2, regarding the cells subjected to the same transfection procedures as in the above except that the aforementioned single-stranded nucleic acid molecule solution was not added and that 1.5 μL of the aforementioned (A) and the aforementioned (B) were added so that the total amount of (A) and (B) would be 100 μL, the expression level of the gene also was measured (mock).

As for the normalized expression level of the TGF-β1 gene, the relative value in the cell introduced with each single-stranded nucleic acid molecule was determined based on the expression level in the cells of the control (−) set as 1.

(3) Results

Figure 5:
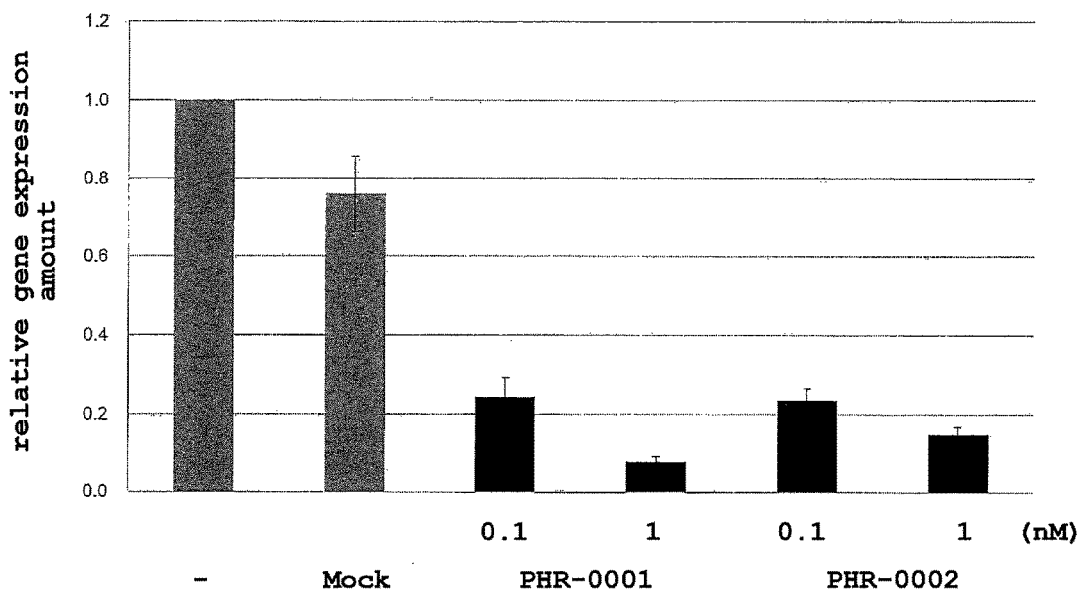
FIG. 5 is a graph showing the relative value of the TGF-β1 amount in Example 1 of the present invention.
Figure 5:
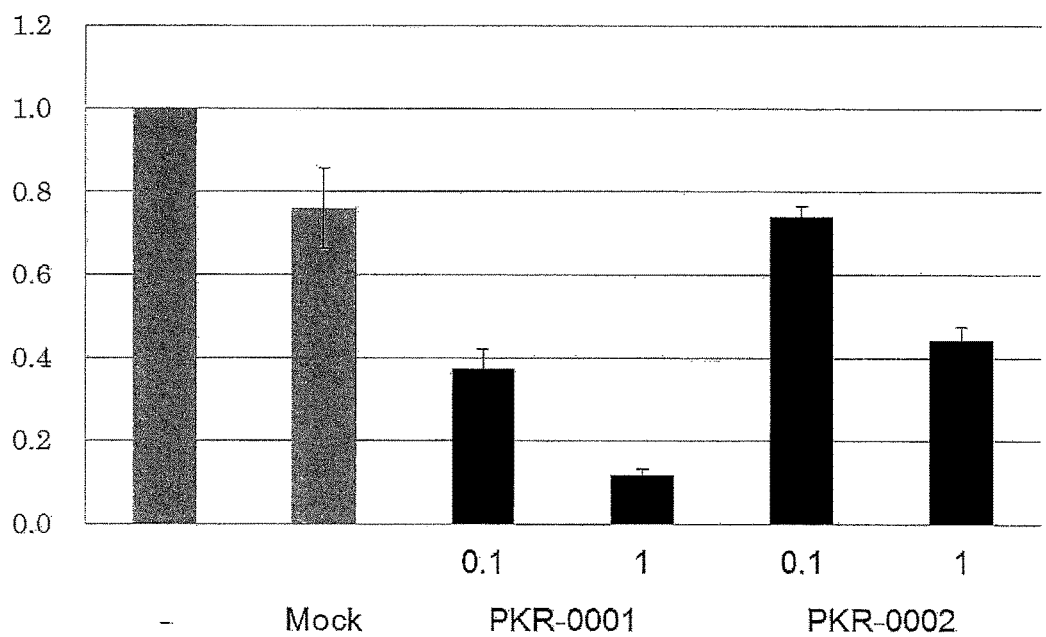

As shown in FIG. 5, the single-stranded nucleic acid molecule of the present invention showed a concentration-dependent strong gene expression inhibitory activity.

Example 2

Acute Lung Injury Inhibitory Effect in Pulmonary Fibrosis Complicated by Acute Lung Injury Model Mouse Using spontaneous pulmonary fibrosis model mouse (human TGF-β1 transgenic mouse described in non-patent documents 6 and 7, hereinafter to be referred to as TG mouse), pulmonary fibrosis and acute lung injury complication model was produced, and an acute lung injury inhibitory effect of the nucleic acid molecule of the present invention was confirmed. The aforementioned effect was confirmed using the protein amount in the bronchoalveolar lavage fluid (BALF) as an index and according to the protocol of BCA Protein Assay Kit (manufactured by Thermo).

(1) Preparation of Nucleic Acid Molecule Solution and LPS Solution

As the nucleic acid molecule, PHR-0001 and PKR-0001 synthesized in the aforementioned Example 1 were used. These nucleic acid molecules were dissolved in sterile physiological saline each at 20 μg/75 μL to give nucleic acid molecule solutions.

On the other hand, lipopolysaccharide (LPS) was dissolved in sterile physiological saline at 100 μg/75 μL to give LPS solution.

(2) Administration to Pulmonary Fibrosis and Acute Lung Injury Complication Model Mouse First, the aforementioned nucleic acid molecule solution (75 μL) was intratracheally administered to mouse by MycroSprayer (MSA-250-M: manufactured by PENNCENTURY). The next day of the intratracheal administration of nucleic acid molecule, the aforementioned LPS solution (75 μL) was similarly administered intratracheally into the trachea of the aforementioned mouse to induce lung injury.

As a negative control for the aforementioned nucleic acid molecule solution, sterile physiological saline (75 μL) was used.

Each administration group is shown below. In each administration group, 5 male mice were used.

Administration Group 1

The next day of administration of sterile physiological saline (75 μL), administration of LPS solution (75 μL)

Administration Group 2

The next day of administration of nucleic acid molecule solution (75 μL), administration of LPS solution (75 μL)

(3) Sampling of Bronchoalveolar Lavage Fluid (BALF) and Measurement of Protein Amount The next day of intratracheal administration of the aforementioned LPS solution or sterile physiological saline, the aforementioned mice were anesthetized with 2% isoflurane and, after whole blood collection and euthanasia, epidermis of the neck was incised and binding tissue was detached to expose trachea. An intravenous indwelling catheter was inserted, advanced by about 9 mm and fixed. The catheter was connected to a 1 mL syringe, sterile physiological saline (2 mL) was slowly added in 3 portions and recovered as BALF sample.

Centrifugation supernatant of the aforementioned BALF sample was measured for the protein amount according to the protocol of BCA Protein Assay Kit (manufactured by Thermo).

(4) Results

Figure 6:
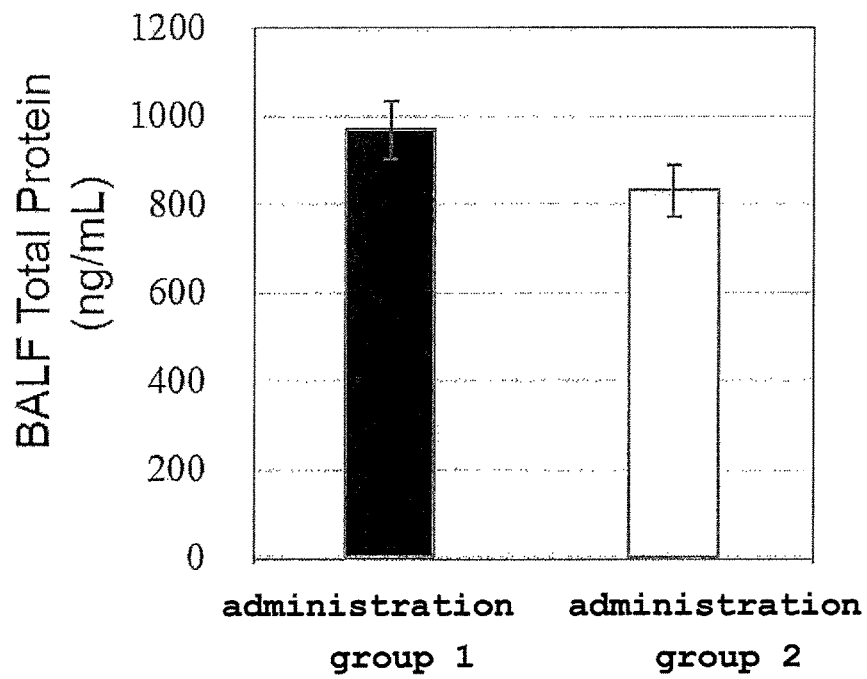
FIG. 6 is a graph showing the protein amount in BALF in Example 2 of the present invention.
Figure 6:
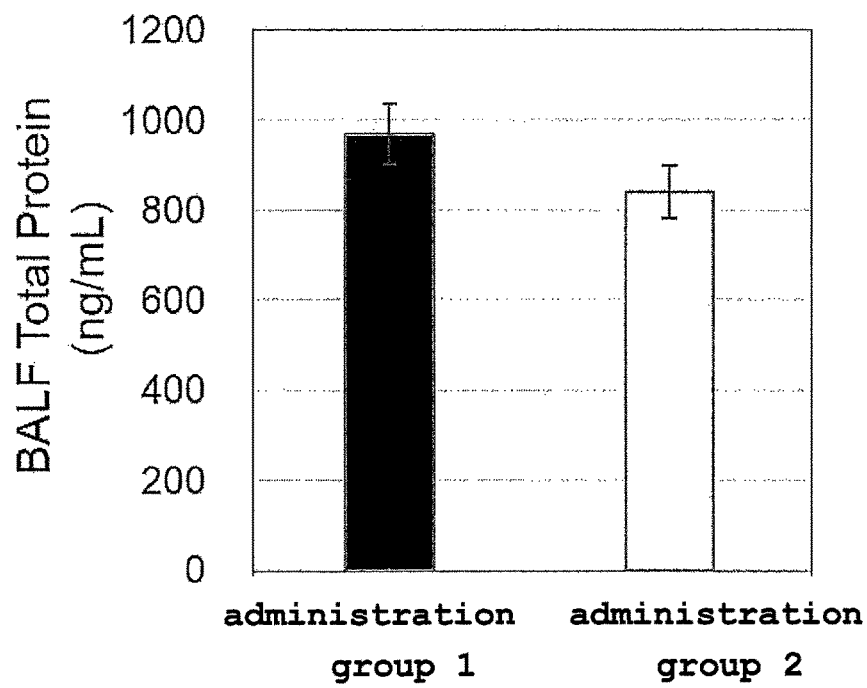

The results thereof are shown in FIG. 6. As compared to administration group 1 administered with sterile physiological saline, administration group 2 administered with single-stranded nucleic acid molecule PHR-0001 (FIG. 6A) or PKR-0001 (FIG. 6B) of the present invention significantly inhibited an increase of the protein amount in BALF. This suggests that the single-stranded nucleic acid molecule of the present invention inhibits the onset of acute lung injury.

Example 3

Pulmonary Fibrosis Inhibitory Effect on Spontaneous Pulmonary Fibrosis Model Mouse Using the aforementioned spontaneous pulmonary fibrosis model mouse, the pulmonary fibrosis inhibitory effect of the nucleic acid molecule of the present invention was confirmed. The aforementioned effect was confirmed according to the method described in non-patent document 7, by using the amount of hydroxyproline in the lung tissue as an index.

(1) Preparation of Nucleic Acid Molecule Solution

As a nucleic acid molecule in the Examples, PHR-0001 synthesized in the aforementioned Example 1 was used.

PHR-0001 was dissolved in sterile physiological saline to 20 μg/75 μL to give a nucleic acid molecule solution.

(2) Administration of Nucleic Acid Molecule to Spontaneous Pulmonary Fibrosis Model Mouse The aforementioned nucleic acid molecule solution was intratracheally administered to mice once/week, total 4 times, by MycroSprayer(R) (MSA-250-M: manufactured by PENNCENTURY).

As a negative control for the aforementioned nucleic acid molecule solution, sterile physiological saline (75 μL) was used.

Each administration group is shown below. In each administration group, 5 male mice were used.

Administration Group 1

Administration of sterile physiological saline (75 µL) to TG mouse

Administration Group 2

Administration of 20 µg/75 µL nucleic acid molecule solution (75 µL) (nucleic acid dose: 1 mg/kg mouse body weight) to TG mouse (3) Sampling of Lung Tissue After 4 weeks from the initial administration, the aforementioned mice were anesthetized with 2% isoflurane, blood samples were collected and the right lobe of the lung was isolated.

(4) Measurement of Amount of Hydroxyproline in Lung Tissue

The aforementioned right lobe of the lung was homogenated by a beads cell disrupter (MS-100: manufactured by TOMY SEIKO CO., LTD.). The aforementioned homogenate was incubated at 110° C. overnight and dried, and disrupted again by the beads cell disrupter. Thereafter, 6N HCl (2 mL) prepared by adding small portions of concentrated hydrochloric acid (100 ml) to distilled water (100 ml) with gentle stirring was added, and a suspension of the disrupted right lobe of the lung was transferred to a screw tube weighed in advance. The tube was plugged, and incubated at 110° C. overnight in a draft. Thereafter, the plug was removed and the tube was incubated at 110° C. overnight in a draft and dried. Thereto was added 2 mL of PBS and the mixture was incubated at 60° C. for 1 hr and passed through a filter to give a sample for the measurement of amount of hydroxyproline. The measurement was performed according to the method described in non-patent document 7.

(5) Results

Figure 7:
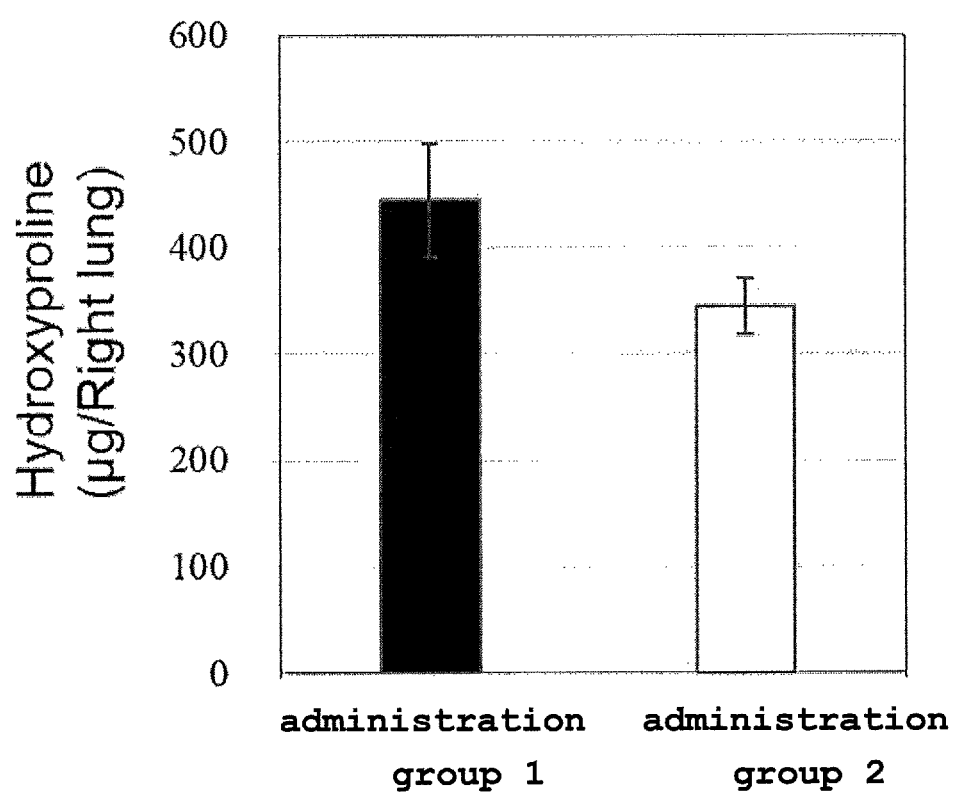
FIG. 7 is a graph showing the amount of hydroxyproline in Example 3 of the present invention.

The results thereof are shown in FIG. 7. As compared to administration group 1 administered with sterile physiological saline, administration group 2 administered with single-stranded nucleic acid molecule PHR-0001 of the present invention significantly inhibited hydroxyproline amount. This suggests that the single-stranded nucleic acid molecule PHR-0001 of the present invention inhibits pulmonary fibrosis in vivo.

While the present invention has been described above with reference to illustrative embodiments, the present invention is by no means limited thereto. Various changes that may become apparent to those skilled in the art may be made in the configuration and specifics of the present invention without departing from the scope of the present invention.

This application is based on patent application Nos. 2014-253148 filed in Japan (filing date: Dec. 15, 2014), 2014-253149 filed in Japan (filing date: Dec. 15, 2014), 2015-121644 filed in Japan (filing date: Jun. 17, 2015), and 2015-121647 filed in Japan (filing date: Jun. 17, 2015), the contents of which are incorporated in full herein.

INDUSTRIAL APPLICABILITY

According to the single-stranded nucleic acid molecule of the present invention, expression of TGF-β1 gene can be inhibited. Therefore, the present invention is effective for the treatment of diseases caused by the expression of TGF-β1 gene such as pulmonary fibrosis, acute lung injury and the like.

The invention claimed is:

1. A single-stranded nucleic acid molecule of the following (A) or (B), comprising a TGF-β1 gene expression inhibitory sequence shown in the following SEQ ID NO: 1 or 2:

```
                                                      (SEQ ID NO: 1)
5'-AUUUCGUUGUGGGUUUCCACC-3'

(SEQ ID NO: 2)
5'-UGUUAUCCCUGCUGUCACAGG-3'
```

(A) a single-stranded nucleic acid molecule consisting of region (X), linker region (Lx) and region (Xc) alone, wherein said region (Xc), said linker region (Lx) and said region (X) are configured in this order from the 5'-side to the 3'-side, said linker region (Lx) has a non-nucleotide structure comprising at least one of a pyrrolidine skeleton and a piperidine skeleton, and at least one of said region (X) and said region (Xc) consists of an additional sequence and said expression inhibitory sequence; wherein the additional sequence is GGAG or GGUG;

(B) a single-stranded nucleic acid molecule comprising region (Xc), linker region (Lx), region (X), region (Y), linker region (Ly) and region (Yc) in this order from the 5'-side to the 3'-side, said region (X) and said region (Y) are linked to form inner region (Z), said region (Xc) is complementary to said region (X), said region (Yc) is complementary to said region (Y), said linker region (Lx) and linker region (Ly) each have a non-nucleotide structure comprising at least one of a pyrrolidine skeleton and a piperidine skeleton, and said inner region (Z) consists of an additional sequence, said expression inhibitory sequence and C, wherein the additional sequence is GGAG or GGUG.

2. The single-stranded nucleic acid molecule according to claim 1, wherein said linker regions (Lx) and (Ly) are represented by the following formula (I):

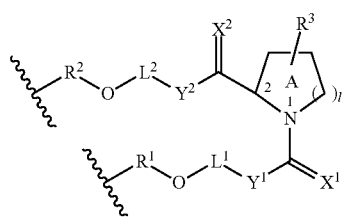

(I)

wherein
$X^1$ and $X^2$ are each independently $H_2$, O, S, or NH;
$Y^1$ and $Y^2$ are each independently a single bond, $CH_2$, NH, O, or S;

$R^3$ is a hydrogen atom or a substituent bonded to C-3, C-4, C-5 or C-6 on ring A;

$L^1$ is an alkylene chain composed of n atoms, and a hydrogen atom on an alkylene carbon atom may or may not be substituted with OH, $OR^a$, $NH_2$, $NHR^a$, $NR^aR^b$, SH, or $SR^a$, or $L^1$ is a polyether chain obtained by substituting at least one carbon atom on said alkylene chain with an oxygen atom, provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain composed of m atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on said alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

l is 1 or 2;

m is an integer in the range from 0 to 30;

n is an integer in the range from 0 to 30;

in ring A, one carbon atom other than C-2 on said ring A may be substituted by nitrogen, oxygen or sulfur, said ring A may contain a carbon-carbon double bond or a carbon-nitrogen double bond, said region (Xc) and said region (X) are each linked to said linker region (Lx) via —$OR^1$— or —$OR^2$—, said region (Yc) and said region (Y) are each linked to said linker region (Ly) via —$OR^1$— or —$OR^2$—, wherein $R^1$ and $R^2$ may or may not be present, and when they are present, $R^1$ and $R^2$ are each independently a nucleotide residue or said structure (I).

3. The single-stranded nucleic acid molecule according to claim 1, wherein a base number (X) of said region (X) and a base number (Xc) of said 5'-side region (Xc) satisfy the conditions of the following formula (3) or the formula (5):

$$X > Xc \qquad (3)$$

$$X = Xc \qquad (5).$$

4. The single-stranded nucleic acid molecule according to claim 3, wherein the base number (X) of said region (X) and the base number (Xc) of said 5'-side region (Xc) satisfy the conditions of the following formula (11):

$$X - Xc = 1, 2 \text{ or } 3 \qquad (11).$$

5. The single-stranded nucleic acid molecule according to claim 1, wherein in said (B), the base number (X) of said region (X), a base number (Y) of said region (Y), the base number (Xc) of said region (Xc) and a base number (Yc) of said region (Yc) satisfy the conditions of the following formula (2):

$$Z \geq Xc + Yc \qquad (2).$$

6. The single-stranded nucleic acid molecule according to claim 1, wherein
in said (B), the base number (X) of said region (X), the base number (Xc) of said region (Xc), the base number (Y) of said region (Y), and the base number (Yc) of said region (Yc) satisfy the conditions of any one of the following (a)-(d):
(a) satisfying the conditions of the following formulae (3) and (4):

$$X > Xc \qquad (3)$$

$$Y = Yc \qquad (4)$$

(b) satisfying the conditions of the following formulae (5) and (6):

$$X = Xc \qquad (5)$$

$$Y > Yc \qquad (6)$$

(c) satisfying the conditions of the following formulae (7) and (8):

$$X > Xc \qquad (7)$$

$$Y > Yc \qquad (8)$$

(d) satisfying the conditions of the following formulae (9) and (10):

$$X = Xc \qquad (9)$$

$$Y = Yc \qquad (10).$$

7. The single-stranded nucleic acid molecule according to claim 6, wherein
in said (a)-(d), a difference between the base number (X) of said region (X) and the base number (Xc) of said region (Xc), and a difference between the base number (Y) of said region (Y) and the base number (Yc) of said region (Yc) satisfy the following conditions:
(a) satisfying the conditions of the following formulae (11) and (12):

$$X - Xc = 1, 2 \text{ or } 3 \qquad (11)$$

$$Y - Yc = 0 \qquad (12)$$

(b) satisfying the conditions of the following formulae (13) and (14):

$$X - Xc = 0 \qquad (13)$$

$$Y - Yc = 1, 2 \text{ or } 3 \qquad (14)$$

(c) satisfying the conditions of the following formulae (15) and (16):

$$X - Xc = 1, 2 \text{ or } 3 \qquad (15)$$

$$Y - Yc = 1, 2 \text{ or } 3 \qquad (16)$$

(d) satisfying the conditions of the following formulae (17) and (18):

$$X - Xc = 0 \qquad (17)$$

$$Y - Yc = 0 \qquad (18).$$

8. The single-stranded nucleic acid molecule according to claim 1, wherein, in said (B), the base number (Xc) of said region (Xc) is 1-11.

9. The single-stranded nucleic acid molecule according to claim 1, wherein, in said (B), the base number (Yc) of said region (Yc) is 1-11.

10. The single-stranded nucleic acid molecule according to claim 1, wherein, in said (A), the base number (Xc) of said region (Xc) is 19-30.

11. The single-stranded nucleic acid molecule according to claim 1, wherein, in said (A), a total of the base number is not less than 40.

12. The single-stranded nucleic acid molecule according to claim 1, wherein, in said (B), a total of the base number is not less than 50.

13. The single-stranded nucleic acid molecule according to claim 1, which is an RNA molecule.

14. The single-stranded nucleic acid molecule according to claim 1, comprising at least one modified residue.

15. The single-stranded nucleic acid molecule according to claim 1, comprising a labeling substance.

16. The single-stranded nucleic acid molecule according to claim 1, comprising a stable isotope.

17. The single-stranded nucleic acid molecule according to claim 1, consisting of
(a) the base sequence shown in SEQ ID NO: 5, the structure shown by the following formula (I-6a):

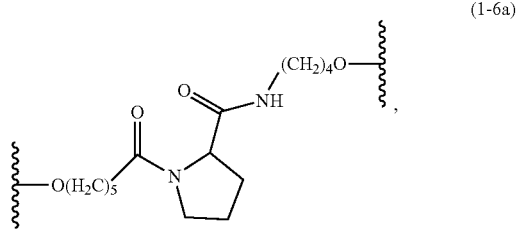

and the base sequence shown in SEQ ID NO: 13, or
(b) the base sequence shown in SEQ ID NO: 6, the structure shown by the formula (I-6a), and the base sequence shown in SEQ ID NO: 14.

18. The single-stranded nucleic acid molecule according to claim 1, consisting of
(a) the base sequence shown in SEQ ID NO: 11, the structure shown by the following formula (I-6a):

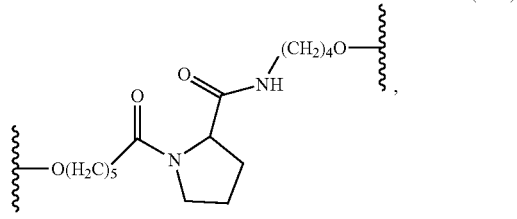

the base sequence shown in SEQ ID NO: 15, the structure shown by the formula (I-6a), and G, or
(b) the base sequence shown in SEQ ID NO: 12, the structure shown by the formula (I-6a), the base sequence shown in SEQ ID NO: 16, the structure shown by the formula (I-6a), and G.

19. A TGF-β1 gene expression inhibitor comprising the single-stranded nucleic acid molecule according to claim 1.

20. A medicament comprising the single-stranded nucleic acid molecule according to claim 1.

21. A method for inhibiting expression of TGF-β1 gene in a cell, a tissue or an organ that express said gene, comprising administering the nucleic acid molecule according to claim 1 to said cell, tissue or organ.

22. A method for treating pulmonary fibrosis, comprising a step of administering the nucleic acid molecule according to claim 1 to a patient.

23. A method for treating acute lung injury, comprising a step of administering the nucleic acid molecule according to claim 1 to a patient.

* * * * *

SEQUENCE LISTING

```
<160> NUMBER OF SEQ ID NOS: 16

<210> SEQ ID NO 1
<211> LENGTH: 21
<212> TYPE: RNA
<213> ORGANISM: Artificial Sequence
<220> FEATURE:
<223> OTHER INFORMATION: Synthetic expression inhibitory sequence

<400> SEQUENCE: 1
auuucguugu ggguuuccac c                                            21

<210> SEQ ID NO 2
<211> LENGTH: 21
<212> TYPE: RNA
<213> ORGANISM: Artificial Sequence
<220> FEATURE:
<223> OTHER INFORMATION: Synthetic expression inhibitory sequence

<400> SEQUENCE: 2
uguuaucccu gcugucacag g                                            21

<210> SEQ ID NO 3
<211> LENGTH: 21
<212> TYPE: RNA
<213> ORGANISM: Artificial Sequence
<220> FEATURE:
<223> OTHER INFORMATION: Synthetic complementary sequence to expression
      inhibitory sequence

<400> SEQUENCE: 3
uggaaaccca caacgaaauc u                                            21
```

<210> SEQ ID NO 4
<211> LENGTH: 21
<212> TYPE: RNA
<213> ORGANISM: Artificial Sequence
<220> FEATURE:
<223> OTHER INFORMATION: Synthetic complementary sequence to expression
      inhibitory sequence

<400> SEQUENCE: 4
ugugacagca gggauaacac a                                              21

<210> SEQ ID NO 5
<211> LENGTH: 23
<212> TYPE: RNA
<213> ORGANISM: Artificial Sequence
<220> FEATURE:
<223> OTHER INFORMATION: Synthetic part of single-stranded nucleic acid
      molecule

<400> SEQUENCE: 5
uggaaaccca caacgaaauc ucc                                            23

<210> SEQ ID NO 6
<211> LENGTH: 23
<212> TYPE: RNA
<213> ORGANISM: Artificial Sequence
<220> FEATURE:
<223> OTHER INFORMATION: Synthetic part of single-stranded nucleic acid
      molecule

<400> SEQUENCE: 6
ugugacagca gggauaacac acc                                            23

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ttgtgcggca gtggttgagc cg                                             22

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
gaagcaggaa aggccggttc atgc                                           24

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
gccacggctg cttccagctc ctc                                            23

<210> SEQ ID NO 10
<211> LENGTH: 25

```
<212> TYPE: DNA
<213> ORGANISM: Artificial Sequence
<220> FEATURE:
<223> OTHER INFORMATION: primer

<400> SEQUENCE: 10
aggtctttgc ggatgtccac gtcac                                          25

<210> SEQ ID NO 11
<211> LENGTH: 24
<212> TYPE: RNA
<213> ORGANISM: Artificial Sequence
<220> FEATURE:
<223> OTHER INFORMATION: Synthetic part of single-stranded nucleic acid
      molecule

<400> SEQUENCE: 11
guggaaaccc acaacgaaau cucc                                           24

<210> SEQ ID NO 12
<211> LENGTH: 24
<212> TYPE: RNA
<213> ORGANISM: Artificial Sequence
<220> FEATURE:
<223> OTHER INFORMATION: Synthetic part of single-stranded nucleic acid
      molecule

<400> SEQUENCE: 12
cugugacagc agggauaaca cacc                                           24

<210> SEQ ID NO 13
<211> LENGTH: 25
<212> TYPE: RNA
<213> ORGANISM: Artificial Sequence
<220> FEATURE:
<223> OTHER INFORMATION: Synthetic part of single-stranded nucleic acid
      molecule

<400> SEQUENCE: 13
ggagauuucg uuguggguuu ccacc                                          25

<210> SEQ ID NO 14
<211> LENGTH: 25
<212> TYPE: RNA
<213> ORGANISM: Artificial Sequence
<220> FEATURE:
<223> OTHER INFORMATION: Synthetic part of single-stranded nucleic acid
      molecule

<400> SEQUENCE: 14
gguguguuau cccugcuguc acagg                                          25

<210> SEQ ID NO 15
<211> LENGTH: 26
<212> TYPE: RNA
<213> ORGANISM: Artificial Sequence
<220> FEATURE:
<223> OTHER INFORMATION: Synthetic part of single-stranded nucleic acid
      molecule

<400> SEQUENCE: 15
ggagauuucg uugugggüuu ccaccc                                         26

<210> SEQ ID NO 16
<211> LENGTH: 26
<212> TYPE: RNA
<213> ORGANISM: Artificial Sequence
```

```
<220> FEATURE:
<223> OTHER INFORMATION: Synthetic part of single-stranded nucleic acid
      molecule

<400> SEQUENCE: 16
gguguguuau cccugcuguc acaggc                                            26
```

UNITED STATES PATENT AND TRADEMARK OFFICE
CERTIFICATE OF CORRECTION

PATENT NO. : 10,337,009 B2
APPLICATION NO. : 15/536006
DATED : July 2, 2019
INVENTOR(S) : Matsumoto et al.

Page 1 of 1

It is certified that error appears in the above-identified patent and that said Letters Patent is hereby corrected as shown below:

In the Claims

Claim 1, Column 41, Line 24, the word "alone" should be deleted after the phrase "region (Xc)"

Signed and Sealed this
Twenty-ninth Day of October, 2019

Andrei Iancu
*Director of the United States Patent and Trademark Office*